United States Patent
Poznansky et al.

(10) Patent No.: US 9,775,816 B2
(45) Date of Patent: Oct. 3, 2017

(54) ELUTING MATRIX AND USES THEREOF

(71) Applicant: The General Hospital Corporation, Boston, MA (US)

(72) Inventors: Mark C. Poznansky, Newton, MA (US); Tao Chen, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/019,449

(22) Filed: Feb. 9, 2016

(65) Prior Publication Data

US 2016/0184234 A1    Jun. 30, 2016

Related U.S. Application Data

(63) Continuation of application No. PCT/US2013/068916, filed on Nov. 7, 2013.

(51) Int. Cl.
| | | |
|---|---|---|
| A61K 38/00 | (2006.01) | |
| A61K 35/00 | (2006.01) | |
| A61K 9/00 | (2006.01) | |
| A61K 9/70 | (2006.01) | |
| A61K 35/39 | (2015.01) | |
| A61K 38/19 | (2006.01) | |
| A61K 9/50 | (2006.01) | |
| A61L 27/20 | (2006.01) | |
| A61L 27/38 | (2006.01) | |
| C08L 5/04 | (2006.01) | |
| C08B 37/00 | (2006.01) | |
| C09D 105/04 | (2006.01) | |

(52) U.S. Cl.
CPC ........ *A61K 9/7007* (2013.01); *A61K 9/5036* (2013.01); *A61K 35/39* (2013.01); *A61K 38/195* (2013.01); *A61L 27/20* (2013.01); *A61L 27/38* (2013.01); *C08B 37/0084* (2013.01); *C08L 5/04* (2013.01); *C09D 105/04* (2013.01)

(58) Field of Classification Search
CPC ...... A61K 35/39; A61K 38/195; A61L 27/009
See application file for complete search history.

(56) References Cited

U.S. PATENT DOCUMENTS

| | | | |
|---|---|---|---|
| 6,448,054 B1 * | 9/2002 | Poznansky | C07K 14/521 424/184.1 |
| 7,141,363 B2 | 11/2006 | Poznansky et al. | |
| 7,176,243 B2 | 2/2007 | Poznansky et al. | |
| 7,192,769 B2 | 3/2007 | Pykett et al. | |
| 7,695,712 B2 | 4/2010 | Poznansky et al. | |
| 7,745,578 B2 | 6/2010 | Poznansky et al. | |

(Continued)

FOREIGN PATENT DOCUMENTS

| | | |
|---|---|---|
| CN | 102065880 A | 5/2011 |
| EP | 1 594 539 | 11/2005 |

(Continued)

OTHER PUBLICATIONS

Duncanson et al., (Biotech Bioengin. Aug. 2013;110(8):2292-2300).*

(Continued)

*Primary Examiner* — Cherie M Stanfield
(74) *Attorney, Agent, or Firm* — Myers Bigel, P.A.

(57) ABSTRACT

CXCL12 polypeptide eluting matrices encapsulating at least one cell are described for use in the treatment of autoimmune disorders.

23 Claims, 16 Drawing Sheets

(56) References Cited

U.S. PATENT DOCUMENTS

| | | | |
|---|---|---|---|
| 7,775,469 | B2 | 8/2010 | Poznansky et al. |
| 7,951,354 | B2 | 5/2011 | Davis et al. |
| 9,381,217 | B2 * | 7/2016 | Garcia .................. A61K 39/44 |
| 2002/0132224 | A1 | 9/2002 | Poznansky et al. |
| 2003/0017141 | A1 | 1/2003 | Poznansky et al. |
| 2006/0263339 | A1 | 11/2006 | Poznansky et al. |
| 2006/0276389 | A1 | 12/2006 | Poznansky et al. |
| 2006/0292689 | A1 | 12/2006 | Poznansky et al. |
| 2007/0009986 | A1 | 1/2007 | Poznansky et al. |
| 2007/0026007 | A1 | 2/2007 | Poznansky et al. |
| 2007/0134657 | A1 | 6/2007 | Poznansky et al. |
| 2008/0064101 | A1 | 3/2008 | Pykett et al. |
| 2008/0300165 | A1 | 12/2008 | Poznansky et al. |
| 2010/0266561 | A1 | 10/2010 | Poznansky et al. |
| 2011/0045077 | A1 * | 2/2011 | Weir .................. A61K 9/1617 424/488 |
| 2011/0129484 | A1 | 6/2011 | Gelfand et al. |
| 2011/0178502 | A1 | 7/2011 | Poznansky et al. |
| 2011/0287949 | A1 | 11/2011 | Poznansky et al. |
| 2012/0329153 | A1 | 12/2012 | Poznansky et al. |

FOREIGN PATENT DOCUMENTS

| | | | |
|---|---|---|---|
| WO | WO 9524929 A2 * | 9/1995 | ........... A61K 9/1272 |
| WO | WO 01/83546 A1 | 11/2001 | |
| WO | WO 03/104256 A2 | 12/2003 | |
| WO | WO 2004/072296 A2 | 8/2004 | |

OTHER PUBLICATIONS

Hick et al., (BMC Develop Biol. Dec. 19, 2009; 9:66. 17 pages).*
Yu et al., (Gene 2006;374:174-179; ePub Apr. 19, 2006).*
Stenvik et al., (J Biom Mat Res. Oct. 2012;100A(10):2803-2812).*
Papeta et al., (Transplantation. Jan. 27, 2007; 83(2):174-183).*
Cheng et al., (Mol Cell Endocrin. Oct. 15, 2011;345(1-2):88-96).*
Liu et al.,(Diabetologica. Aug. 2011; 54(8):2067-2076).*
Zhao et al., (Biochem Biophys Res Comm. 2010;399:629-636).*
Gombotz et al., (Adv Drug Deliv Rev. May 4, 1998;31(3):267-285).*
Wang et al., (Biomaterials. 2011. 32(21):4903-4913).*
Stabler et al., (Biomaterials. Jun. 2001;22(11):1301-10).*
International Search Report (PCT/ISA/210) issued in PCT Application No. PCT/US2013/068916 dated Sep. 25, 2014 (3 pages).
Papeta et al., "Long-Term Survival of Transplanted Allogenic Cells Engineered to Express a T Cell Chemorepellent", Transplantation, Jan. 27, 2007, p. 174-183, vol. 83, No. 2.
Shapiro et al., "International Trial of the Edmonton Protocol for Islet Transplantation", The New England Journal of Medicine, Sep. 28, 2006, p. 1318-1330, vol. 355, No. 13.
Kaddis et al., "Human Pancreatic Islets and Diabetes Research", JAMA, Apr. 15, 2009, p. 1580-1587, vol. 301, No. 15.
Robertson, "Islet Transplantation as a Treatment for Diabetes—A Work in Progress", The New England Journal of Medicine, Feb. 12, 2004, p. 694-705, vol. 350.
Jalili et al., "Local Expression of Indoleamine 2,3 Dioxygenase in Syngeneic Fibroblasts Significantly Prolongs Survival of an Engineered Three-Dimensional Islet Allograft", Diabetes, Sep. 2010, p. 2219-2227, vol. 59.
Vaithilingam et al., "The Humanized NOD/SCID Mouse as a Preclinical Model to Study the Fate of Encapsulated Human Islets", The Review of Diabetic Studies, 2010, p. 62-73, vol. 7, No. 1.
Mallett et al., "Alginate Modification Improves Long-Term Survival and Function of Transplanted Encapsulated Islets", Tissue Engineering: Part A, 2009, p. 1301-1309, vol. 15, No. 6.
Sakata et al., "Encapsulated Islets Transplantation: Past, Present and Future", World Journal of Gastrointestinal Pathophysiology, Feb. 15, 2012, p. 19-26, vol. 3, No. 1.
Poznansky et al., "Thymocyte Emigration is Mediated by Active Movement Away from Stroma-Derived Factors", Journal of Clinical Investigation, Apr. 2002, p. 1101-1110, vol. 109, No. 8.
Poznansky et al., "Active Movement of T Cells Away From a Chemokine", Nature Medicine, May 2000, p. 543-548, vol. 6, No. 5.
Khattar et al., "Novel Sphingosine-1-Phosphate Receptor Modulator KRP203 Combined with Locally-Delivered Regulatory T-Cells Induces Permanent Acceptance of Pancreatic Islet Allografts", Transplantation, Apr. 15, 2013, p. 919-927, vol. 95, No. 7.
Vianello et al., "Fugetaxis: Active Movement of Leukocytes Away from a Chemokinetic Agent", J Mol Med, Sep. 3, 2005, p. 752-763, vol. 83.
Righi et al., "CXCL12/CXCR4 Blockade Induces Multimodal Anti-Tumor Effects that Prolong Survival in an Immunocompetent Mouse Model of Ovarian Cancer", Cancer Res, Aug. 15, 2011, p. 5522-5534, vol. 71, No. 16.
Liu et al., "Stromal Cell-Derived factor-1 Promotes Survival of Pancreatic Beta Cells by the Stabilisation of Transcription Factor 7-Like 2 (TCF7L2)", Biabetologia, Aug. 2009, p. 1589-1598, vol. 52, No. 8.
Pelletier et al., "Presentation of Chemokine SDF-1a by Fibronectin Mediates Directed Migration of T Cells", Blood, Oct. 15, 2000, p. 2682-2690, vol. 96, No. 8.
Datta et al., "Differential Effects of Immunosuppressive Drugs on T-Cell Motility", American Journal of Transplantation, 2006, p. 2871-2883, vol. 6.
Yu et al., "Early Expression of Anti-insulin Autoantibodies of Humans and the NOD Mouse: Evidence of Early Determination of Subsequent Diabetes", PNAS, Feb. 15, 2000, p. 1701-1706, vol. 97, No. 4.
Eisenbarth, "Insulin Autoimmunity: Immunogenetics/Immunopathogenesis of Type 1A Diabetes", Ann. N.Y. Acad. Sci., 2003, p. 109-118, vol. 1005.
Bonifacio et al., "International Workshop on Lessons from Animal Models for Human Type 1 Diabetes: Identification of Insulin but Not Glutamic Acid Decarboxylase or IA-2 as Specific Autoantigens of Humoral Autoimmunity in Non-obese Diabetic Mice", Diabetes, Nov. 2001, p. 2451-2458, vol. 50.
Wang et al., "Engineering Chemoattractant Gradients Using Chemokine-Releasing Polysaccharide Microspheres", Biomaterials, Jul. 2011, p. 4903-4913, vol. 32, No. 21.
Yano et al., "Stromal Cell-Derived Factor-1 (SDF-1)/ CXCL12 Attenuates Diabetes in Mice and Promotes Pancreatic B-Cell Survival by Activation of the Prosurvival Kinase Akt", Diabetes, Dec. 2007, p. 2946-2957, vol. 56.
Ma et al., "Impaired B-Lymphopoiesis, Myelopoiesis, and Derailed Cerebellar Neuron Migration in CXCR4- and SDF-1-Deficient Mice", Proc. Natl. Acad. Sci. USA, Aug. 1998, p. 9448-9453, vol. 95.
Netelenbos et al., "Proteoglycans Guide SDF-2-Induced Migration of Hematopoietic Progenitor Cells", Journal of Leukocyte Biology, Aug. 2002, p. 353-362, vol. 72.
Piccirillo, "Regulatory T cells in Heath and Disease", Cytokine, 2008, p. 395-401, vol. 43.
Xia et al., "Prevention of Allograft Rejection by Amplification of Foxp3+CD4+CD25+ Regulatory t Cells", Transl Res., Feb. 2009, p. 60-70, vol. 153, No. 2.
Wood, "Regulatory T Cells in Transplantation", Transplantation Proceedings, 2011, p. 2135-2136, vol. 43.
Feng et al., "Interferon-y Conditioning Ex Vivo Generates CD25+CD62I+Foxp3+ Regulatory T cells That Prevent Allograft Rejection: Potential Avenues for Cellular Therapy", Transplantation, 2008, p. 578-589, vol. 86.
Richer et al., "Immunomodulation of Antigen Presenting Cells Promotes Natural Regulatory T Cells That Prevent Autoimmune Diabetes in NOD Mice", PloS One, Feb. 2012, vol. 7, Issue 2, e31153.
Tonkin et al., "Regulatory T Cells Prevent Transfer of Type 1 Diabetes in NOD Mice Only When Their Antigen is Present in Vivo", J Immunol, 2008, p. 4516-4522, vol. 181.
Hire et al., "FoxP3+, and not CD25+, T Cells Increase Post-Transplant in Islet Allotransplant Recipients Following Anti-CD25+ rATG Immunotherapy", Cellular Immunology, 2012, p. 83-88, vol. 274.

(56) References Cited

OTHER PUBLICATIONS

Shi et al., "Endogenous Expansion of Regulatory T Cells Leads to Long-term Islet Graft Survival in Diabetic NOD Mice", American Journal of Transplantation, 2012, p. 1124-1132, vol. 12.
Francis et al., "Induction of Transplantation Tolerance Converts Potential Effector T Cells Into Graft-Protective Regulatory t Cells", Eur. J. Immunol., 2011, p. 726-738, vol. 41.
Chen et al., "CD4+CD25+ Regulatory T-Cells Inhibit the Islet Innate Immune Response and Promote Islet Engraftment", Diabetes, Apr. 2006, p. 1011-1021, vol. 55.
Marek et al., "Coating Human Pancreatic Islets with CD4+CD25 highCD127- Regulatory Cells as a Novel Approach for the Local Immunoprotection", Annals of Surgery, Sep. 2011, p. 512-519, vol. 254, No. 3.
Yolcu et al., "Pancreatic Islets Engineered with SA-FasL Protein Establish Robust Localized Tolerance by Inducing T Regulatory Cells in Mice", J Immunol., Dec. 1, 2011, p. 5901-5909, vol. 187, No. 11.
Jaafar et al., "Correlation of CXCL12 Expression and FoxP3+ Cell Infiltration with Human Papillomavirus Infection and Clinicopathological Progression of Cervical Cancer", The American Journal of Pathology, Oct. 2009, p. 1525-1535, vol. 175, No. 4.
Zou et al., "Bone Marrow Is a Reservoir for CD4+CD25+ Regulatory T Cells That Traffic Through CXCL12/CXCR4 Signals", Cancer Research, Nov. 15, 2004, p. 8451-8455, vol. 64.
Moon et al., "LPS-Induced Migration of Peritoneal B-1 Cells is Associated with Upregulation of CXCR4 and Increased Migratory Sensitivity to CXCL12", J Korean Med Sci, 2012, p. 27-35, vol. 27.
Leach, "Putting Killer Cells in Reverse: The Hidden Power of CXCL12" Insulin Nation, Published May 14, 2013.
Vianello et al., "A CXCR4-Dependent Cemorepellent Signal Contributes to the Emigration of Mature Single-Positive CD4 Cells From the Fetal Thymus", The Journal of Immunology, 2005, p. 5115-5125, vol. 175.
Vianello et al., "Murine B16 melanomas Expressing High Levels of the Chemokine Stromal-Derived Factor-1/CXCL12 Induce Tumor-Specific T Cell Chemorepulsion and Escape from Immune Control", J Immunol, 2006, p. 2902-2914, vol. 176.
Brainard et al., "Migration of Antigen-Specific T Cells Away from CXCR4-Binding Human Immunodeficiency Virus Type 1 gp120", Journal of Virology, May 2004, p. 5184-5193, vol. 78, No. 10.
Gombotz et al., "Protein release from Alginate Matrices", Advanced Drug Delivery Reviews, 1998, p. 267-285, vol. 31.
Yu et al., "Identification and Expression of Novel Isoforms of Human Stromal Cell-Derived Factor 1", Gene, 2006, p. 174-179, vol. 374.
Vianello et al., "Method for Quantitation of Leukocyte Chemotaxis and Fugetaxis", Method Mol. Biol., 2005, p. 115-124, vol. 616.
Preliminary Report on Patentability (PCT/ISA 373) and Written Opinion (PCT/ISA/237) issued in PCT Application No. PCT/US2013/068916 dated May 10, 2016 (7 pages).
Gibly et al. "Advancing islet transplantation: from engraftment to the immune response", *Diabetologia* 54:2494-2505 (2011).
Sakata et al. "Encapsulated islets transplantation: Past, present and futue", *World J Gastrointest Pathophysiol* 3(1):19-26 (2012).
Vaithilingam et al. "Islet Transplantation and Encapsulation: An Update on Recent Developments", *The Review of Diabetic Studies* 8(1):51-67 (2011).
Extended European Search Report corresponding to European Application No. 13896941.5 dated May 4, 2017.

\* cited by examiner

ELUTING MATRIX AND USES THEREOF

The instant application contains a Sequence Listing which has been submitted in ASCII format via EFS-Web and is hereby incorporated by reference in its entirety. Said ASCII copy, created on Mar. 8, 2016, is named 68770US_ST25.txt and is 5.94 kilo bytes in size.

BACKGROUND OF THE INVENTION

Transplantation is a potentially curative approach for individuals with autoimmune disorders such as type I diabetes mellitus (T1DM), but its utility is limited by acute and chronic immune rejection of transplanted cells (N. Papeta et al. Transplantation 83, 174 (Jan. 27, 2007); A. M. Shapiro et al. The New England journal of medicine 355, 1318 (Sep. 28, 2006); J. S. Kaddis et al. JAMA 301, 1580 (Apr. 15, 2009); R. P. Robertson. The New England journal of medicine 350, 694 (Feb. 12, 2004); R. B. Jalili et al. Diabetes 59, 2219 (September, 2010); and V. Vaithilingam, The review of diabetic studies: 7, 62 (Spring, 2010)). Immune rejection is currently managed by continuous systemic immune suppression, an approach that has not shown significant long-term effectiveness, while exposing recipients to increased risks of infection and cancer (A. G. Mallett, G. S. Korbutt. Tissue engineering. Part A 15, 1301 (June, 2009); N. Sakata et al. World journal of gastrointestinal pathophysiology 3, 19 (Feb. 15, 2012); M. C. Poznansky et al. The Journal of clinical investigation 109, 1101 (April, 2002); and M. C. Poznansky et al. Nature medicine 6, 543 (May, 2000)). Alternative therapies that can overcome the need for systemic immunosuppression through the induction of local anatomic site specific immune modulation would be desirable.

SUMMARY OF THE INVENTION

CXCL12 polypeptides can repel effector T-cells while recruiting immune-suppressive regulatory T-cells to an anatomic site. It has now been determined that CXCL12 is capable of overcoming both acute and chronic immune destruction of an implanted matrix in a site specific manner, abrogating the need for concurrent systemic immune suppression.

In one aspect, provided herein relates to compositions comprising at least one cell encapsulated in a CXCL12 polypeptide eluting matrix.

In some embodiments, the CXCL12 polypeptide eluting matrix can be characterized by a release of the CXCL12 polypeptide at a rate sufficient to repel effector cells. For example, in some embodiments, the CXCL12 polypeptide eluting matrix can be characterized by a release of the CXCL12 polypeptide at a rate of at least about 1.0 ng/mL/hr. In some embodiments, the CXCL12 polypeptide can be released from the CXCL12 polypeptide eluting matrix at a rate of at least about 1.5 ng/mL/hr, at least about 2 ng/mL/hr, at least about 2.5 ng/mL/hr, at least about 3 ng/mL/hr, at least about 4 ng/mL/hr, at least about 5 ng/mL/hr or higher. In some embodiments, the CXCL12 polypeptide can be released at a rate of about 1.0 ng/mL/hr to about 3 ng/mL/hr. In some embodiments, the CXCL12 polypeptide can be released at a rate of about 1.75 ng/ml/hr. By way of example only, the composition described herein can be characterized by an ability of repelling effector cells in vitro in a boyden chamber.

The CXCL12 polypeptide can be present in the eluting matrix at any concentration. In some embodiments, the concentration of the CXCL12 polypeptide can be optimized, e.g., for a desired release rate of the CXCL12 polypeptide from the eluting matrix and/or its release duration. In some embodiments, the CXCL12 polypeptide can be present in the matrix at a concentration of about 100 ng/mL. In some embodiments, the CXCL12 polypeptide can be present in the matrix at a concentration of about 100 ng/mL to about 1 µg/mL. In some embodiments, the concentration of CXCL12 polypeptide within the eluting matrix can be maintained at a concentration of about 100 ng/ml to about 1 µg/ml for about 3 months to about 2 years. In some embodiments, the concentration of the CXCL12 polypeptide within the eluting matrix can be maintained at about 100 ng/mL to about 1 µg/mL for about 3 months to about 2 years upon implantation of the composition in a subject. In some embodiments, the maintained concentration of CXCL12 polypeptide within the matrix can be about 100-200 ng/ml.

To form a CXCL12 polypeptide eluting matrix, the CXCL12 polypeptides can be pre-loaded into the eluting matrix or produced in situ in the eluting matrix. For example, in some embodiments, the CXCL12 polypeptides within the CXCL12 polypeptide eluting matrix can be provided by CXCL12 polypeptide-secreting cells or cells engineered to secrete CXCL12 polypeptides. In one embodiment, the CXCL12 polypeptides within the matrix can be provided by the islet cells within the matrix.

In some embodiments, the CXCL12 polypeptides present in the eluting matrix can comprise an amino acid sequence based on the species of a subject to be treated. For example, in some embodiments, the CXCL12 polypeptide can comprise a human CXCL12 polypeptide.

The CXCL12 polypeptide eluting matrix can be characterized by various matrix structures. For example, in some embodiments, the CXCL12 polypeptide eluting matrix can form a capsule. In some embodiments, the CXCL12 polypeptide eluting matrix can be in a form of solid or foam matrix. In some embodiments, the CXCL12 polypeptide eluting matrix can form multi-compartment or multi-layered matrix. In these embodiments, the cell(s) and the CXCL12 polypeptide can be present in the same or different compartments or layers of the CXCL12 polypeptide eluting matrix.

The thickness of the CXCL12 polypeptide eluting matrix can be varied to suit the needs of various applications. By way of example only, the thickness of the CXCL12 polypeptide eluting can be adjusted for fast release or slow release of the CXCL12 polypeptide from the eluting matrix. In some embodiments, the matrix thickness can be about 200-about 500 microns.

The cell(s) encapsulated in the CXCL12 polypeptide eluting matrix can be collected or derived from any source, any species, and/or any tissue type. Additionally or alternatively, the cell(s) encapsulated in the CXCL12 polypeptide eluting matrix can be differentiated from stem cells to specific cell types. In some embodiments, the cell(s) encapsulated in the CXCL12 polypeptide eluting matrix can be autologous. In some embodiments, the cell(s) encapsulated in the CXCL12 polypeptide eluting matrix can be allogeneic cell(s) or xenogeneic cell(s).

In some embodiments, the cell(s) encapsulated in the CXCL12 polypeptide eluting matrix can retain their function and/or activity for a desired period of time, e.g., upon implantation of the compositions in a subject. In some embodiments, the cell(s) can retain their function and/or activity for at least about 1 month or longer, including, e.g., at least about 2 months, at least about 3 months or longer. In some embodiments, the cell(s) can retain their function and/or activity for at least about 1 month or longer after implantation of the composition described herein in a subject.

Depending on types of cells encapsulated in the CXCL12 polypeptide eluting matrix, the cells can perform different functions and/or activity. In some embodiments, the cell(s) encapsulated in the CXCL12 polypeptide eluting matrix can regulate blood glucose level in a subject. For example, upon implantation, the cell(s) encapsulated in the CXCL12 polypeptide eluting matrix can release insulin in response to surrounding or ambient glucose level. In these embodiments, the cell(s) encapsulated in the CXCL12 polypeptide eluting matrix can comprise an islet cell. The islet cell can be an insulin producing cell, an islet cell derived from an induced pluripotent stem (iPS) cell, a porcine islet cell, a human islet cell, or any combinations thereof.

In some embodiments, the cell(s) encapsulated in the CXCL12 polypeptide eluting matrix can be removed. In some embodiments, the cell(s) can be provided to the CXCL12 polypeptide eluting matrix in vivo.

The CXCL12 polypeptide eluting matrix can comprise at least one or more biocompatible biopolymers. The biocompatible polymers can be biodegradable or non-degradable. The biocompatible polymers can be carbohydrate-based, protein-based, and/or synthetic. In some embodiments, the biocompatible polymers can be selected such that they are inert to encapsulated cells (e.g., no stimulation or inhibition of cell signaling), and are permeable to the CXCL12 polypeptide to be eluted and optionally permeable to a target molecule to be sensed. In some embodiments, the biocompatible polymers can be selected such that the average pore size of the eluting matrix excludes molecules that are greater than about 130 kD.

In some embodiments, the CXCL12 polypeptide eluting matrix can comprise an alginate gel. The alginate gel can comprise mannuronic acid (M) and guluronic acid (G) at a (M/G) ratio selected to achieve properties specific for individual applications. Exemplary properties of the alginate gel that can be optimized by the M/G ratio include, but are not limited to, molecular weight cut-off, porosity, pore size, gel strength, and/or release profile of the CXCL12 polypeptide.

In some embodiments, the alginate gel can comprise a high mannuronic acid content. In some embodiments, the alginate gel can comprise mannuronic acid (M) and guluronic acid (G) at a (M/G) ratio of about 1 or greater than 1. In some embodiments, the concentration of the alginate gel can vary from about 1% w/v to about 5% w/v. In some embodiments, the concentration of the alginate gel can be about 2% w/v.

In some embodiments, the composition described herein can further comprise a layer of cells that can express the CXCL12 polypeptide. In some embodiments, the CXCL12 polypeptide-expressing cells can comprise mesothelial cells.

In some embodiments, the composition described herein can further comprise an absorbable layer of a CXCL12 polypeptide over the eluting matrix.

In some embodiments, the compositions can be formulated to be injectable compositions.

In various embodiments, the compositions described herein can be implanted or injected at a target site in a subject for treatment of a disease or disorder. In some embodiments, the compositions can comprise at least one islet cell encapsulated in a CXCL12 polypeptide eluting matrix. Accordingly, in some embodiments, the composition, e.g., for treatment of diabetes, can be characterized as a composition comprising allograft or xenograft islet cells encapsulated in a CXCL12 polypeptide eluting matrix wherein the matrix is characterized by: (a) a matrix thickness from 200-500 microns, and a concentration of CXCL12 polypeptide in the matrix from about 100 ng/ml to about 1 µg/ml; (b) a porosity such that agents regulating serum glucose concentration in a subject having type I diabetes diffuse through the matrix; and (c) insulin production by the islet cells based on the interaction of the agents with the islet cells, the insulin being released through the matrix and at a rate sufficient to regulate the serum concentration or blood level of glucose in the subject. The matrix thickness, CXCL12 concentration and/or elution rate can be tuned to inhibit degradation of the islet cells for a period of at least or up to about 4 months, thereby providing control of the blood glucose levels in the subject during the period. In some embodiments, the matrix thickness, CXCL12 concentration and/or elution rate can be tuned to inhibit degradation of the islet cells for a period of about 6 months or longer.

In another aspect, methods for providing islet cells to a subject in need thereof are also described herein. The method comprises implanting one or more embodiments of the compositions described herein into the subject, wherein the islet cells regulate blood glucose levels in the subject for a period of time. By way of example only, the islet cells encapsulated in the CXCL12 polypeptide eluting matrix, upon implantation in the subject, can regulate blood glucose levels in the subject for a period of at least about 1 month or longer, including, e.g., at least about 2 months, at least about 3 months, at least about 6 months, at least about 9 months, at least about 1 year, at least about 2 years or longer.

In some embodiments, the islet cells encapsulated in the CXCL12 polypeptide eluting matrix can maintain or restore the fasting serum concentration of glucose in the subject at a blood level of between about 80 mg/dl and about 120 mg/dl.

In some embodiments, the CXCL12 polypeptide eluting matrix is not degraded by effector T-cells or macrophages.

In some embodiments, regulatory T-cells can be present at the site of implantation. In some embodiments, effector-T cells can be absent from the site of implantation. By way of example only, the presence of the regulatory T-cells or the absence of the effector T-cells can be measured by flow cytometry or immunohistochemistry.

In some embodiments, the subject can receive repeated implantation of a composition comprising at least one islet cell encapsulated in a CXCL12 polypeptide eluting matrix.

A further aspect described herein provides methods for replenishing islet cells in a subject in need thereof having an existing xenograft islet cell deposit. The method comprises (a) assessing the half-life of the islet cells existing in the subject; (b) providing islet cells to the subject such that the aggregated half-life of the islet cells is at a therapeutic level to provide control of the glucose levels in the subject for a period of time; and (c) repeating steps (a) and (b) based on the half-life of the islet cells. In some embodiments, the half-life of the islet cells exiting in the subject can be assessed or estimated by monitoring changes in the blood glucose level in a subject. For example, a return of blood glucose to a diabetic state can be indicative of a need to replenish islet cells in the subject.

Compositions comprising a CXCL12 polypeptide eluting matrix are also provided herein. The matrix can be characterized by: (a) a porosity such that CXCL12 polypeptide is slowly eluted from the composition and penetrates an active site of an autoimmune disease; (b) an agent that renders the composition non-migratory after administration such that a substantial portion of the matrix remains located in and about the site of administration; wherein the CXCL12 polypeptide concentration and elution rate are selected to inhibit further development of said autoimmune disease. In some embodiments, the compositions described herein can be administered by injection. In these embodiments, the compositions can be formulated to be injectable compositions.

Other features and advantages of the invention will be apparent from the detailed description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

FIG. 1A is a survival curve of the proportion of allograft islets after transplantation. BALB/C islets were exposed to CXCL12 at concentrations of about 100 ng/ml and about 1 µg/ml or PBS alone and transplanted under the renal capsule of STZ-treated diabetic C57BL/6 recipients. Return to hyperglycemia was considered to be an indicator of graft rejection, while sustained normoglycemia was considered to be an indicator of allograft survival. Coating of islets with about but not 100 ng/ml, of CXCL12 significantly delayed graft rejection compared to PBS controls (p=0.012, log-rank test)(12 animals per group). FIG. 1B is a set of images characterizing allograft islets. Representative Hematoxylin and Eosin (H&E) staining of subcapsular islet graft sites showed reduced mononuclear cell infiltration in ~1 µg/ml CXCL12-coated islets compared to uncoated controls (left panels). Insulin staining of ~1 µg/ml CXCL12 and PBS coated islet graft areas showed a greater number of functional islets and level of insulin secretion in CXCL12 coated islets compared to PBS controls (middle panels). Additionally, fluorescent staining showed evidence of CXCL12 staining in CXCL12-coated islets compared to controls (right panels). Costaining of CXCL12 and insulin is shown in a brighter shade. FIG. 1C is a bar graph quantifying the number of CD3+ cells present in the islet grafts based on CD3 immunostaining, and shows that there is significantly decreased infiltration of CD3+ cells into the graft area in ~1 µg/ml CXCL12-coated grafts (p=0.001) compared to uncoated controls (6 animals per group). FIG. 1D is a bar graph quantifying the number of FoxP3+ cells present in the islet grafts based on FoxP3 staining, and shows that there is significantly greater FoxP3+ cell localization to 1 µg/ml CXCL12-coated grafts than to PBS controls (p=0.0016) (n=6).

FIG. 2A is a survival curve of the proportion of mice remaining non-diabetic after transplantation of CXCL12-coated or uncoated islets and with or without CsA treatment. There was a significant reduction in graft survival time when CXCL12 coating was combined with CsA treatment at 23 days post transplantation (p=0.0245, log-rank test). FIG. 2B is a set of images of immunohistochemical staining for CD3, FoxP3, and insulin in each condition studied. The staining was consistent with survival data shown in FIG. 2A and shows decreased CD3+ and increased FoxP3+ cell infiltration, as well as greater expression of insulin, in CXCL12 coated islets compared to CXCL12+ CsA islets. FIG. 2C is a bar graph showing quantification of the number of CD3+ and FoxP3+ cells in islet grafts in each of the three conditions studied. Significantly decreased numbers of FoxP3+ cells (p=0.0188) and increased numbers of CD3+ cells (p=0.0002) were observed in CXCL12+CsA grafts compared to CXCL12 coating alone.

FIG. 3A shows BrdU incorporation in the splenocytes compared to negative staining control (shaded). FIG. 3B shows that there was no difference in BrdU incorporation into CD4 T-cells from mice which received uncoated (line) and CXCL12-coated islets (shaded). FIG. 3C is a bar graph showing the average number of allo-specific CD4 T-cells per spleen in each mouse group and indicating that coating islets with CXCL12 does not modulate the systemic immune response to allogeneic tissue. (n=3)

FIG. 4A is a survival curve of the proportion of mice remaining non-diabetic after transplantation; there is a significant difference between CXCL12 and PBS exposed islets (Log-Rank test, p=0.017), indicating prolonged survival and function of transplanted syngeneic CXCL12 coated islets. FIG. 4B is a bar graph quantifying the number of CD3+ cells in the islet grafts, and shows that there was a significant decrease in CD3+ cell infiltration into CXCL12 coated islet grafts (p=0.0081). FIG. 4C is a bar graph quantifying the number of FoxP3+ cells in the islet grafts, and shows that there was significantly increased localization of FoxP3+ cells to CXCL12 coated islets than to PBS exposed islets (p=0.0019).

FIG. 5A is a survival curve of the proportion of mice remaining non-diabetic after transplantation; there is no significant difference between CXCL12 and PBS exposed islets (Log-Rank test, p=0.24). FIG. 5B is a set of images of H&E staining (left panels) showing decreased mononuclear cell infiltration into islet grafts coated with 1 µg/ml CXCL12 (left panels) and of immunofluorescent staining for insulin and CXCL12 (right panels) showing increased levels of both proteins in CXCL12 coated grafts. FIG. 5C is a bar graph quantifying the number of CD3+ cells in the islet grafts, and shows that although there was no difference in survival, there was a significant decrease in CD3+ cell infiltration into CXCL12 coated islet grafts (p=0.0015). FIG. 5D is a bar graph quantifying the number of FoxP3+ cells in the islet grafts, and shows that there was significantly increased localization of FoxP3+ cells to CXCL12 coated islets than to PBS exposed islets.

FIG. 6A is a line graph showing kinetics of CXCL12 release from cell-free calcium cross-linked ~3.3% alginate encapsulant over time in vitro. The concentration of CXCL12 in un-cross-linked sodium alginate was 1 µg/ml; a significant amount of CXCL12 was lost in the $CaCl_2$ cross-linking solution (n=3). There were no differences in CXCL12 release profiles for alginate concentrations of 1.5% to 3.3% (data not shown). Initial release rate of CXCL12 from 1.5% alginate capsules during the first 24 hours was 1.75 ng/ml/hr+/−0.01 ng/ml/hr and after four days stabilized at a release rate of 0.18 ng/ml/hr+/−0.002 ng/ml/hr. FIG. 6B is a bar graph showing electrostatic interaction between CXCL12 and barium cross linked alginate capsule. The left panel shows that a significantly lower amount of CXCL12 remained in beads following incubation with 1M NaCl compared to incubation in the absence of NaCl. The right panel shows that a significantly higher amount of CXCL12 was eluted in the medium following incubation with 1M NaCl compared to incubation in NaCl free medium (n=3, *p<0.05). FIG. 6C is a bar graph of caspase-3 activity showing that CXCL12 incorporation significantly reduces caspase-3 activity in encapsulated murine islets (p=0.0019 for ~100 ng/ml CXCL12 and p=0.00028 for ~1 µg/ml CXCL12 versus control). Murine islets were encapsulated with Ca-LVM or Ca-LVM incorporating either ~100 ng/ml or ~1 µg/ml CXCL12 (Ca-LVM-CXCL12) and then cultured in vitro for 48 hours, after which caspase-3 activity was determined. FIG. 6D is a survival plot showing the proportion of allograft islets after transplantation. Incorporation of 1 µg/ml CXCL12 into a Ca-LVM encapsulant delays rejection of allogeneic islets (n=12) for both groups, p=0.0237, Gehan-Breslow-Wilcoxon test). FIG. 6E is a survival plot of the proportion of allograft islets after transplantation. Incorporation of ~1 µg/ml CXCL12 also delays rejection of encapsulated allogeneic islets transplanted into allo-sensitized NOD/LtJ mice (Ca-LVM Capsule, n=7; Ca-LVM-CXCL12 Capsule, n=9; p=0.0066, Gehan-Breslow-Wilcoxon test). FIG. 6F is a survival plot the proportion of allograft islets after transplantation. Incorporation of ~1 µg/ml CXCL12 significantly delays rejection of encapsulated porcine xenogeneic islets transplanted into diabetic C57BL/6 mice (p=0.0389, log-rank test). Control and experimental groups: Ca-LVM Capsule, Ca-LVM-10 ng/ml CXCL12 Capsule, Ca-LVM-100 ng/ml CXCL12 Capsule (n=6), Ca-LVM-1 µg/ml CXCL12 Capsule (*p<0.01)(Group size=6)(Gehan-Breslow-Wilcoxon test).

FIG. 7A and FIG. 7C are bar graphs showing migratory responses of CD3+CD8+T cells. FIG. 7B and FIG. 7D are bar graphs showing migratory response of CD3+CD4+ CD25hi T-cells. The cell migratory responses were quantitated in response to CXCL12, islets coated with CXCL12 (I-CXCL12) and islets encapsulated with CXCL12(E-CXCL12). CXCL12 was used at a concentration of ~1 µg/ml in all three settings. CD8+ and CD4+CD25Hi T-cells underwent low levels of chemotaxis to ~1 µg/ml CXCL12 (M/CXCL12) and islets coated or encapsulated with CXCL12. CD8+, but not CD4+CD25Hi, T-cells underwent fugetaxis or chemorepulsion in response to CXCL12 coated or encapsulated islets Minimal levels of both chemotaxis and fugetaxis were detected for CD8+ or CD4+CD25Hi T-cells exposed to islets that were not coated with CXCL12 (I-Cont) or encapsulated islets alone (E-Cont). (ns=non-significant; * p<0.05;  p<0.005, Student's test). To explain these different migratory responses, CXCR4 expression on CD4+, CD8+, and regulatory T-cells was compared. FIG. 7E shows an example of gating strategy for CD8+ and regulatory T-cells. FIG. 7F is a plot showing mean fluorescence intensity (MFI) of CXCR4 expression. Percentage of each population expressing CXCR4 was calculated, and a representative histogram in FIG. 7**G illustrates the increased expression by Treg cells of CXCR4 compared to CD4+ CD25- and CD8+ T-cells (p<0.0001, Student's t test).

DETAILED DESCRIPTION OF THE INVENTION

Definitions

Figure 1A:
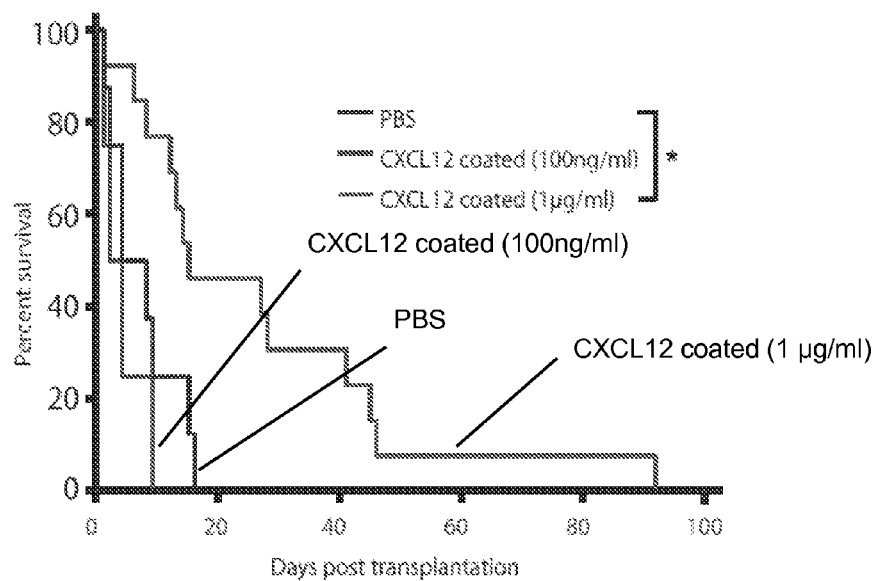
FIGS. 1A-1D show that coating of alloislets with a high concentration of CXCL12 delays rejection.

Unless otherwise defined, all technical and scientific terms used herein have the same meaning as commonly understood by one of ordinary skill in the art to which this invention belongs. In case of conflict, the present application, including definitions will control.

The term "alginate" as used herein is also known as "alginic acid" and generally refers to a carbohydrate polymer (e.g., a polysaccharide) comprising at least two uronate sugars.

The term "allogeneic" means belonging to or obtained from the same species.

The term "allograft" refers to a graft of cells or tissue obtained from the same species.

The term "xenogeneic" means belonging to or obtained from a different species.

The term "xenograft" refers to a graft of cells or tissue obtained from a different species.

The term "effector T-cell" refers to a differentiated T-cell capable of mounting a specific immune response by releasing cytokines.

The term "regulatory T-cell" refers to a T-cell that reduces or suppresses the immune response of B-cells or of other T-cells to an antigen.

By "CXCL12 or SDF-1 polypeptide" is meant a protein or fragment thereof that binds a CXCL12 specific antibody and that has chemotaxis or fugetaxis activity. Chemotaxis or fugetaxis activity is determined by assaying the direction of T cell migration (e.g., toward or away from an agent of interest). See, for example, Poznansky et al., Nature Medicine 2000, 6:543-8.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods of the Invention

Compositions of the invention are directed to CXCL12 polypeptide eluting matrices encapsulating at least one cell. CXCL12 polypeptides are known in the art. See, for example, Poznansky et al., Nature Medicine 2000, 6:543-8. Note that the terms CXCL12 and SDF-1 may be used interchangeably. In one embodiment, a CXCL12 polypeptide has at least about 85%, 90%, 95%, or 100% amino acid sequence identity to NP_001029058 and has chemokine or fugetaxis activity. Exemplary SDF1 Isoforms are provided in Table 1 (below):

TABLE 1

HUMAN SDF1 ISOFORMS

| Name | Accession Number | Accession Number Versions | Sequence | SEQ ID NO. |
|---|---|---|---|---|
| SDF-1 Alpha | NP_954637 | NP_954637.1 GI: 40316924 | MNAKVVVVLV LVLTALCLSD GKPVSLSYRC PCRFFESHVA RANVKHLKIL NTPNCALQIV ARLKNNNRQV CIDPKLKWIQ EYLEKALNK | SEQ ID NO: 1 |
| SDF-1 Beta | P48061 | P48061.1 GI: 1352728 | MNAKVVVVLV LVLTALCLSD GKPVSLSYRC PCRFFESHVA RANVKHLKIL NTPNCALQIV ARLKNNNRQV CIDPKLKWIQ EYLEKALNKR FKM | SEQ ID NO: 2 |
| SDF-1 Gamma | NP_001029058 | NP_001029058.1 GI: 76563933 | MNAKVVVVLV LVLTALCLSD GKPVSLSYRC PCRFFESHVA RANVKHLKIL NTPNCALQIV ARLKNNNRQV CIDPKLKWIQ EYLEKALNKG RREEKVGKKE KIGKKKRQKK RKAAQKRKN | SEQ ID NO: 3 |
| SDF-1 Delta | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNNL ISAAPAGKRV IAGARALHPS PPRACPTARA LCEIRLWPPP EWSWPSPGDV | SEQ ID NO: 4 |
| SDF-1 Epsilon | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNNC | SEQ ID NO: 5 |
| SDF-1 Phi | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNKI WLYGNAETSR | SEQ ID NO: 6 |

In another embodiment, the sequence of an exemplary CXCL12/SDF-1 polypeptide is mnakvvvvlvlvltalclsdgkpvslsyrcperffeshvaranvkhlkilntpncalqivarlknnnrqvcidpklkwiqeylekalnkg rreekvgkkekigkkkrqkkrkaaqkrkn (SEQ ID NO:3).

In yet another embodiment, a CXCL12 polypeptide has at least about 85%, 90%, 95%, or 100% amino acid sequence identity to a CXCL12 isoform delta polypeptide and has chemokine or fugetaxis activity. The sequence of an exemplary CXCL12 isoform delta polypeptide MNAKVVVVLVLVLTALCLSDGKPVSLSYRCPCRFFESHVARANVKHLKILNTPNCA LQIVARLKNNNRQVCIDPKLKWIQEYLEKALNNLISAAPAGKRVIAGARALHPSPPR ACPTARALCEIRLWPPP EWSWPSPGDV (SEQ ID NO:4).

CXCL12 polypeptide eluting matrices are characterized, for example, by a release of the CXCL12 polypeptide at a rate of at least about 1.0 ng/mL/hr, e.g., between about 1.0 ng/mL/hr to about 3 ng/mL/hr. In specific embodiments, the CXCL12 polypeptide is released at a rate of about 1.75 ng/ml/hr. The CXCL12 polypeptide is present in the matrix at a concentration of at least about 100 ng/mL, e.g., between about 100 ng/ml to about 1 µg/ml. In specific embodiments, the CXCL12 polypeptide is present in the matrix at a concentration of between about 100 ng/ml to about 1 µg/ml. for about 3 months to about 2 years. Concentrations, release rates and durations will vary according to the selected cell type and disorder to be treated and the selection of appropriate parameters will be known or apparent to those skilled in the art. In general, the CXCL12 polypeptide is released at a rate sufficient to repel effector T-cells from a specific anatomic site. The ability of a CXCL12 polypeptide eluting matrix to repell effector T-cells can be assessed in vitro, using a boyden chamber assay, as previously described in Poznansky et al., Journal of clinical investigation, 109, 1101 (2002).

Eluting matrices can comprise biocompatible polymers known in the art that are inert to encapsulated cells (i.e., no stimulation or inhibition of cell signaling), and are permeable to the CXCL12 polypeptide to be eluted and the molecule to be sensed (e.g. glucose). The matrix thickness is about 200-about 500 microns and in specific embodiments, forms a capsule around the cells. Biocompatible polymers can be biodegradable or non-degradable. The biocompatible polymer can be carbohydrate-based, protein-based, and/or synthetic, e.g., PLA. Biocompatable materials suitable for use in matrices include, but are not limited to, poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, nylon silicon, poly(styrene-block-butadiene), polynorbornene, and hydrogels. Other suitable polymers can be obtained by reference to The Polymer Handbook, 3rd edition (Wiley, N. Y., 1989). Combinations of these polymers may also be used.

In one embodiment, CXCL12 polypeptide eluting matrices of the invention further comprise a secondary layer of cells that express the CXCL12 polypeptide, such as mesothelial cells. In other embodiments, the outer layer of the matrix further comprises an absorbable layer of a CXCL12 polypeptide.

In one embodiment, the eluting matrix comprises an alginate (e.g., alginic acid) and generally refers to a carbohydrate polymer (e.g., a polysaccharide) comprising at least two uronate sugars. The uronate sugars can include, but are not limited to, salts of mannuronic acid (or mannuronate), salts of guluronic acid (or guluronate), and/or isomers thereof. In some embodiments, the alginate can be a linear carbohydrate polymer (e.g., a polysaccharide) comprising mannuronate, guluronate and/or isomers thereof. In some embodiments, alginate can be a co-carbohydrate polymer of mannuronate, guluronate, and/or isomers thereof.

As used herein, the term "isomers" refers to compounds having the same molecular formula but differing in structure. Isomers which differ only in configuration and/or conformation are referred to as "stereoisomers." The term "isomer" is also used to refer to an enantiomer. The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Enantiomers generally have identical physical properties, such as melting points and boiling points, and also have identical spectroscopic properties. Enantiomers can differ from each other with respect to their interaction with plane-polarized light and with respect to biological activity. Accordingly, in some embodiments, the salts of mannuronic acid (or mannuronate) can comprise β-D-mannuronate. In some embodiments, the salts of guluronic acid (or guluronate) can comprise α-L-guluronate.

In some embodiments, alginate can be a block polymer comprising at least one or more homopolymeric regions of mannuronate (M-blocks), at least one or more homopolymeric regions of guluronate (G-blocks), at least one or more regions of alternating structure of mannuronate and guluronate (MG-blocks or GM-blocks).

The proportion, distribution and/or length of these blocks can, in part, determine the chemical and/or physical properties of an alginate gel. For example, the relative content of G and M monomers in the alginate polymers can affect, e.g., but not limited to, pore size, stability and biodegradability, gel strength and elasticity of alginate gels. Without wishing to be bound by theory, lower G content relative to M content in the alginate polymers can generally result in more biodegradable gels. Gels with higher G content alginate can generally have larger pore sizes and/or stronger gel strength relative to gels with higher M content alginate, which have smaller pore sizes and lower gel strength. In some embodiments, one or more of the alginate polymers of the alginate matrix can comprise a M-block content of at least about 10 wt %, at least about 20 wt %, at least about 30 wt %, at least about 40 wt %, at least about 50 wt %, at least about 60 wt %, at least about 70 wt %, at least about 80 wt %, at least about 90 wt % or more. In some embodiments, one or more of the alginate polymers of the alginate matrix can comprise a G-block content of at least about 10 wt %, at least about 20 wt %, at least about 30 wt %, at least about 40 wt %, at least about 50 wt %, at least about 60 wt %, at least about 70 wt %, at least about 80 wt %, at least about 90 wt % or more. In some embodiments, one or more of the alginate polymers of the alginate matrix can comprise a GM- and/or MG-block content of at least 10 wt %, at least about 20 wt %, at least about 30 wt %, at least about 40 wt %, at least about 50 wt %, at least about 60 wt %, at least about 70 wt %, at least about 80 wt %, at least about 90 wt % or more.

In some embodiments, one or more of the alginate polymers of the alginate matrix can comprise a mannuronic acid to guluronic acid (M/G) ratio of about 0.01 to about 100, or about 0.1 to about 50, or about 0.5 to about 25, or about 1 to about 20. In some embodiments, one or more of the alginate polymers of the alginate matrix can have a M/G ratio of about 1 to about 100, or about to about 50, or about 1 to about 25, or about 1 to about 20, or about 1 to about 10, or about 1 to about 5.

In some embodiments, one or more of the alginate polymers of the alginate matrix can comprise a guluronic acid to mannuronic acid (G/M) ratio of no more than 1.5 or no more than 1. For example, in some embodiments, one or more of the alginate polymers of the alginate matrix can have a G/M ratio of about 1.5. In some embodiments, one or more of the alginate polymers of the alginate matrix can have a G/M ratio of about 1. In some embodiments, one or more of the alginate polymers of the alginate matrix can have a G/M ratio of less than 1.5, including, e.g., less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.1, less than 0.05, less than 0.01, less than 0.0075, less than 0.005, less than 0.001 or lower. In some embodiments, one or more of the alginate polymers of the alginate matrix can have a G/M ratio of less than 1, including, e.g., less than 0.9, less than 0.8, less than 0.7, less than 0.6, less than 0.5, less than 0.4, less than 0.3, less than 0.2, less than 0.1, less than 0.05, less than 0.01, less than 0.0075, less than 0.005, less than 0.001, less than 0.0001, or lower.

In some embodiments, one or more of the alginate polymers of the alginate matrix can comprise a guluronic acid to mannuronic acid (G/M) ratio of at least about 1.5 or higher. For example, in some embodiments, one or more of the alginate polymers of the alginate matrix can have a G/M ratio of about 1.5. In some embodiments, one or more of the alginate polymers of the alginate matrix can have a G/M ratio of greater than 1.5, including, e.g., greater than 2, greater than 2.5, greater than 3, greater than 3.5, greater than 4, greater than 4.5, greater than 5, greater than 6, greater than 7, greater than 8, greater than 9, greater than 10, greater than 15, greater than 20, greater than 30, greater than 40, greater than 50, greater than 60, greater than 70, greater than 80, greater than 90, greater than 100 or higher.

The average molecular weight of alginate polymers can affect, e.g., gelling time, pore size, gel strength and/or elasticity of gels. Alginate polymers can have average molecular weights ranging from about 2 kDa to 10000 kDa. Without wishing to be bound by theory, lower molecular weight of the alginate polymer can generally result in more biodegradable gels. In some embodiments, the alginate polymers of the alginate matrix can have an average molecular weight of about 5 kDa to about 10,000 kDa, or about 10 kDa to about 5000 kDa, or about 25 kDa to about 2500 kDa, or about 50 kDa to about 1000 kDa, or about 50 kDa to about 500 kDa, or about 50 kDa to about 250 kDa. In some embodiments, the alginate polymers of the alginate matrix can have an average molecule weight of about 5 kDa to about 350 kDa. In some embodiments, the alginate polymers of the alginate matrix can have an average molecule weight of about 2 kDa to about 100 kDa. In some embodiments, the alginate polymers of the alginate matrix have an average molecule weight of about 50 kDa to about 500 kDa. In some embodiments, the alginate polymers of the alginate matrix have an average molecule weight of about 50 kDa to about 300 kDa. In some embodiments, the alginate polymers of the alginate matrix have an average molecule weight of about 75 kDa to about 200 kDa. In some embodiments, the alginate polymers of the alginate matrix have an average molecule weight of about 75 kDa to about 150 kDa. In some embodiments, the alginate polymers of the alginate matrix have an average molecule weight of about 150 kDa to about 250 kDa. In some embodiments, the alginate polymers of the alginate matrix have an average molecule weight of about 100 kDa to about 1000 kDa.

In some embodiments, the alginate polymers of the alginate matrix can have an average molecular weight of less than 75 kDa or lower. In some embodiments, the alginate polymers of the alginate matrix can have an average molecular weight of at least about 75 kDa, at least about 80 kDa, at least about 90 kDa, at least about 100 kDa, at least about 110 kDa, at least about 120 kDa, at least about 130 kDa, at least about 140 kDa, at least about 150 kDa, at least about 160 kDa, at least about 170 kDa, at least about 180 kDa, at least about 190 kDa, at least about 200 kDa, at least about 250 kDa, at least about 300 kDa, or higher.

In one embodiment, the alginate polymers of the alginate matrix has an average molecular weight of about 75 kDa to about 200 kDa, with a guluronic acid to mannuronic acid (G/M) ratio of about 1. In one embodiment, the alginate polymers of the alginate matrix has an average molecular weight of about 75 kDa to about 200 kDa, with a guluronic acid to mannuronic acid (G/M) ratio of less than 1.

Without limitations, the molecular weight can be the peak average molecular weight (Mp), the number average molecular weight (Mn), or the weight average molecular weight (Mw).

The alginate can be derived from any source and/or produced by any art-recognized methods. In some embodiments, the alginate can be derived from stem and/or leaves of seaweeds or kelp. In some embodiments, the alginate can be derived from green algae (Chlorophyta), brown algae (Phaeophyta), red algae (Rhodophyta), or any combinations thereof. Examples of seaweeds or kelps include, but are not limited to, various types of *Laminaria* (e.g., but not limited to, *Laminaria hyperborea*, *Laminaria digitata*, and *Laminaria japonica*), *Lessonia nigrescens*, *Lessonia trabeculata*, *Durvillaea antarctica*, *Ecklonia maxima*, *Macrocystis pyrifera*, *Ascophyllum nodosum*, and any combinations thereof.

In some embodiments, the alginate can be a bacterial alginate, e.g., produced by a microbial fermentation using bacteria. Examples of bacteria that can be used in alginate production include, but are not limited to, *Pseudomonas* (e.g., *Pseudomonas Aeruginosa*) and *Azotobacter* (e.g., *Azobacter Vinelandii*). In some embodiments, the bacteria can produce a polysaccharide polymer with a structure resembling alginate, for example, differing in that there are acetyl groups on a portion of the C2 and C3 hydroxyls.

In some embodiments, the alginate can be modified. In some embodiments, the alginate can be chemically modified. For example, a chemically modified alginate can comprise propylene glycol alginate (PGA). In some embodiments, PGA can be made by contacting a partially neutralized alginic acid with propylene oxide gas under pressure. The propylene oxide can react exothermically with the alginic acid to form a mixed primary/secondary ester.

In some embodiments, the alginate can be of clinical grade, e.g., suitable for use in vivo. In some embodiments, the alginate can be purified prior to use for cell encapsulation. See, e.g., Mallet and Korbutt, Tissue Eng Part A. 2009. 15(6):1301-1309. In some embodiments, the alginate can have low endotoxin. For example, endotoxins can be present in the alginate in an amount of no more than 150 EU/gram, no more than 100 EU/gram, no more than 75 EU/gram, no more than 50 EU/gram, no more than 25 EU/gram, no more than 20 EU/gram, no more than 10 EU/gram, no more than 5 EU/gram, no more than 1 EU/gram, no more than 0.5 EU/gram, no more than 0.1 EU/gram.

Any art-recognized alginate can be used in the methods of various aspects described herein. Examples of alginates that can be used in the compositions described herein include, without limitations, sodium alginate (sodium salt of alginic acid), postassium alginate (potassium salt of alginic acid), calcium alginate, magnesium alginate, triethanolamine alginate, PGA, and any combinations thereof. In some embodiments, soluble alginate can be in the form of mono-valent salts including, without limitation, sodium alginate, potassium alginate and ammonium alginate. In some embodiments, the alginate can be calcium alginate. In one embodiment, calcium alginate can be made from sodium alginate from which the sodium salt has been removed and replaced with calcium. Alginates described in and/or produced by the methods described in the International Patent Application Nos. WO 2007/140312; WO 2006/051421; WO2006/132661; and WO1991/007951 and U.S. Pat. No. 8,481,695 can also be used in the compositions and methods of various aspects described herein. In some embodiments, commercially-available alginates, e.g., obtained from FMC BioPolymer and Novamatrix, can also be in the compositions and methods of various aspects described herein.

Alginate generally forms a gel matrix in the presence of divalent ions and/or trivalent ions. Non-limiting examples of divalent or trivalent ions that can be used to form alginate gels include calcium ions, barium ions, strontium ions, copper ions, zinc ions, magnesium ions, manganese ions, cobalt ions, lead ions, iron ions, aluminum ions, and any combinations thereof.

In some embodiments, the alginate matrix can be covalently crosslinked. Examples of covalent crosslinking agents that can be used to covalently crosslink alginate include, but are not limited to, carbodiimides, allyl halide oxides, dialdehydes, diamines, and diisocyanates.

Eluting matrix formulations of the invention include those suitable for injection, infusion or implantation (subcutaneous, intravenous, intramuscular, intraperitoneal, intradermal, parenteral, rectal, and/or intravaginal or the like), inhalation, oral/nasal or topical administration. The formulations may conveniently be presented in unit dosage form and may be prepared by any methods well known in the art of pharmacy. The amount of CXCL12 polypeptide which can be combined in a dosage form will vary depending upon the host being treated, the particular mode of administration, e.g., injection or implantation. Formulations of this invention can be prepared according to any method known to the art for the manufacture of pharmaceuticals and can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, emulsions, creams, lotions, gels, on patches and in implants.

CXCL12 polypeptide eluting matrices of the invention encapsulate at least one cell. Encapsulated cells can include, but are not limited to, stem cells, neuronal cells, smooth or skeletal muscle cells, myocytes, fibroblasts, chondrocytes, adipocytes, fibromyoblasts, ectodermal cells, including ductile and skin cells, hepatocytes, kidney cells, liver cells, cardiac cells, pancreatic cells, islet cells, cells present in the intestine, osteoblasts and other cells forming bone or cartilage, and hematopoietic cells. In specific embodiments, the cell is an insulin producing cell, such as an islet cell (e.g., a porcine islet cell, a human islet cell or an islet cell derived from a stem or iPS cell).

Eluting matrices of the invention are refillable CXCL12 polypeptide delivery devices implanted or otherwise inserted within a patient. For example, the matrix may comprise a needle or catheter entry port so that cells can be infused or removed without removing the matrix from the patient. Alternatively, the eluting matrices can be repeatedly administered to a subject (e.g., a "sensitized subject"), without associated immune rejection.

CXCL12 polypeptide eluting matrices of the invention are useful in the treatment of autoimmune diseases including, but not limited to, rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulo-nephritis, autoimmune hepatitis, and systemic lupus erythematosus.

In one embodiment, CXCL12 polypeptide eluting matrices of the invention can be formulated with islet cells for use in the treatment of diabetes. Diabetes is a condition in which a person has a high blood sugar (glucose) level as a result of the body either not producing enough insulin, or because body cells do not properly respond to the insulin that is produced. In healthy persons, blood glucose levels are maintained within a narrow range, primarily by the actions of the hormone insulin. Insulin is released by pancreatic beta-cells at an appropriate rate in response to circulating glucose concentrations, the response being modulated by other factors including other circulating nutrients, islet innervation and incretin hormones. Insulin maintains glucose concentrations by constraining the rate of hepatic glucose release to match the rate of glucose clearance.

Insulin thus enables body cells to absorb glucose, to turn into energy. If the body cells do not absorb the glucose, the glucose accumulates in the blood (hyperglycemia), leading to various potential medical complications. Accordingly, diabetes is characterized by increased blood glucose resulting in secondary complications such as cardiovascular diseases, kidney failure, retinopathy and neuropathy if not properly controlled.

Two major pathophysiologies are related to increase glycemia. The first is an autoimmune attack against the pancreatic insulin-producing beta-cells (Type 1 diabetes) whilst the second is associated to poor beta-cell function and increased peripheral insulin resistance (Type 2 diabetes). Similar to Type 1, beta-cell death is also observed in Type 2 diabetes. Type 1 and often Type 2 diabetes requires the person to inject insulin.

Type 1 DM is typically characterized by loss of the insulin-producing beta-cells of the islets of Langerhans in the pancreas leading to insulin deficiency. This type of diabetes can be further classified as immune-mediated or idiopathic. The majority of Type 1 diabetes is of the immune-mediated nature, where beta-cell loss is a T-cell mediated autoimmune attack. Type 2 DM is characterized by beta-cell dysfunction in combination with insulin resistance. The defective responsiveness of body tissues to insulin is believed to involve the insulin receptor. Similar to Type 1 diabetes an insufficient beta cell mass is also a pathogenic factor in many Type 2 diabetic patients. In the early stage of Type 2 diabetes, hyperglycemia can be reversed by a variety of measures and medications that improve insulin secretion and reduce glucose production by the liver. As the disease progresses, the impairment of insulin secretion occurs, and therapeutic replacement of insulin may sometimes become necessary in certain patients.

Regulatory T-cells are a subset of CD4+ T cells originated from the thymus, which are generally known to play a significant role in maintenance of tolerance. Regulatory T-cells actively play a role in immune modulation, and suppress alloimmune responses of transplant rejection (C. A. Piccirillo. Cytokine 43, 395 (September, 2008); G. Xia et al. Translational research: the journal of laboratory and clinical medicine 153, 60 (February, 2009); K. J. Wood. Transplantation proceedings 43, 2135 (July-August, 2011); and G. Feng et al. Transplantation 86, 578 (Aug. 27, 2008)). Regulatory T-cells prevent murine autoimmune diabetes and control autoreactive destruction of transplanted islets (M. J. Richer et al. PloS one 7, e31153 (2012) and D. R. Tonkin et al. Immunol 181, 4516 (Oct. 1, 2008)). Islet transplantation represents a potentially curative approach to diabetes, however, in previous studies of islet transplantation, systemic immune suppression could not achieve long-term control of blood glucose levels due to immune-mediated rejection of transplanted islets. Incorporation of CXCL12 into a matrix encapsulating transplanted islets provides both a physical and a biological barrier to cell-mediated and humoral anti-islet immunity. The CXCL12 polypeptide repels effector T-cells and recruits immune-suppressive regulatory T-cells, while reducing or eliminating the need for systemic immunosuppression. Accordingly, in one embodiment, CXCL12 polypeptide eluting matrices of the invention are useful for the regeneration, replacement or substitution (partial or wholly) of at least part of the pancreas of a patient deficient in pancreatic cells, particularly beta-cells without concomitant immunosuppression. Any patient whose pancreas does not produce sufficient insulin, or indeed any insulin, may benefit from such therapy. Insufficient insulin production includes the production of lower levels of insulin compared to a normal (healthy) subject, but it also includes subjects who produce insulin levels that are comparable to normal (healthy) subjects but who require higher insulin levels, for example due to insulin resistance, excessive food consumption, morbid obesity and the like.

CXCL12 polypeptide eluting matrices of the invention selectively recruit regulatory T-cells, thereby prolonging survival of the implanted matrix and providing protection from immune destruction in even a sensitized host. Accordingly, CXCL12 polypeptide eluting matrices of the invention are retrievable, and can be repeatedly administered, if desired, without immune system rejection. Furthermore, CXCL12 polypeptide eluting matrices of the invention provide sustained islet survival and continuous production of CXCL12 polypeptides from the encapsulated islets, for at least about 1 month to about 2 years. During this time, the fasting serum concentration of glucose in the subject is maintained at a blood level of between about 80 mg/dl and about 120 mg/dl. Accordingly, CXCL12 polypeptide eluting matrices of the invention are particularly useful in the treatment of diabetes.

In a specific embodiment, a CXCL12 polypeptide eluting matrix for use in treating diabetes comprises about 1.5 to about 2% w/v of a high mannuronic acid, calcium cross-linked alginate, about 100 ng/ml to about 1 µg/ml of a CXCL12 polypeptide and at least one islet cell, wherein the CXCL12 polypeptide is released at a rate of between about 1.0 ng/ml/hr to about 3 ng/ml/hr. An exemplary encapsulation procedure begins with preparation of the islet cells, by mixing donor islets with 2 mL filtered dithizone/PBS. 80 mg of alginate-LVM (Pronova UP LVM Sodium Alginate) is mixed in 5 mL 300 mOsmo NaCl until dissolved. About 800 to about 1000 islets are spun down in cRPM for 3 minutes at 300 rpm ×G, re-suspended in DMEM and spun again at 300 rpm×G for 3 minutes. A 1 mL syringe can be used to mix 0.75 mL alginate with islets. Alginate and islets can be loaded into a 60 mL syringe using 18 g needle. The loaded syringe is placed into the encapsulator, having the voltage set at the maximum (e.g., 1.21 kV), the frequency set at 1500 and the amplitude set at maximum. After encapsulation, stir capsules for about 5 minutes in 300 mOsmo CaCl2 and filter capsules into fresh beaker, wash and culture with DMEM.

The present invention is additionally described by way of the following illustrative, non-limiting Examples that provide a better understanding of the present invention and of its many advantages.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Islet transplantation represents a potentially curative approach to Type I Diabetes. However, the islet transplantation generally requires systemic immune suppression to control immune-mediated rejection of transplanted islets and there is a limited human islet supply. The following Examples show that the chemokine, CXCL12, can repel effector T-cells while recruiting immune-suppressive regulatory T-cells (Tregs) to an anatomic site, and coating or encapsulating donor islets with CXCL12 can induce local immune-isolation and protect an allo- or xenograft without systemic immune suppression. In the following Examples, islet transplantation was performed in murine models of insulin-dependent diabetes. Coating of islets with CXCL12 or microencapsulation of islets with alginate incorporating the chemokine, CXCL12, resulted in prolonged allo- and xenoislet survival and function, as well as a selective increase in Treg infiltration. These data as shown below indicate the use of CXCL12 as coating or a component of alginate encapsulant to induce local immune-isolation for allo- or xenoislet transplantation while abrogating the need for systemic immunosuppression.

Example 1

Direct Coating of Alloislets with CXCL12 Polypeptide

Figure 1B:
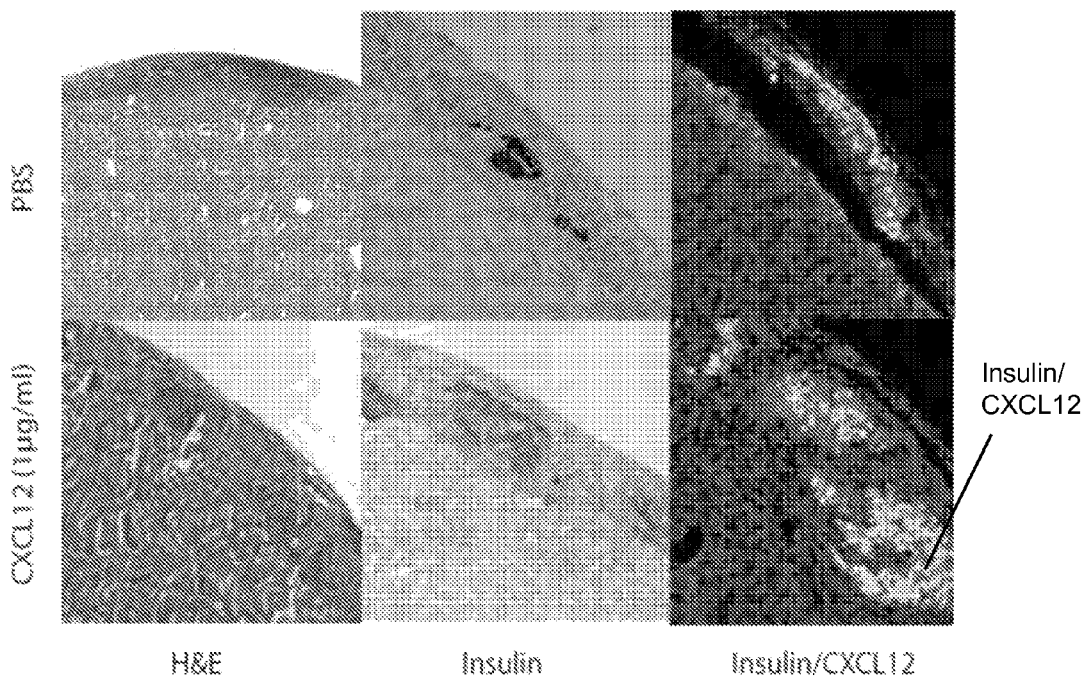
Figure 1C:
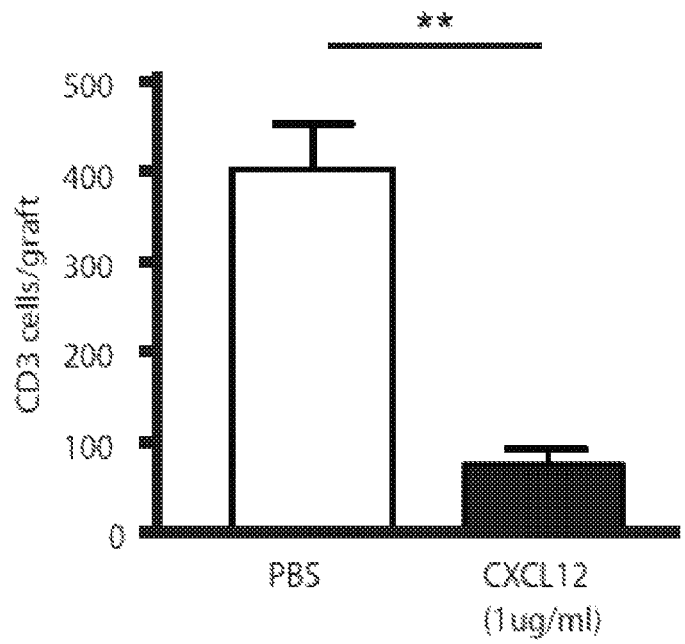
Figure 1D:
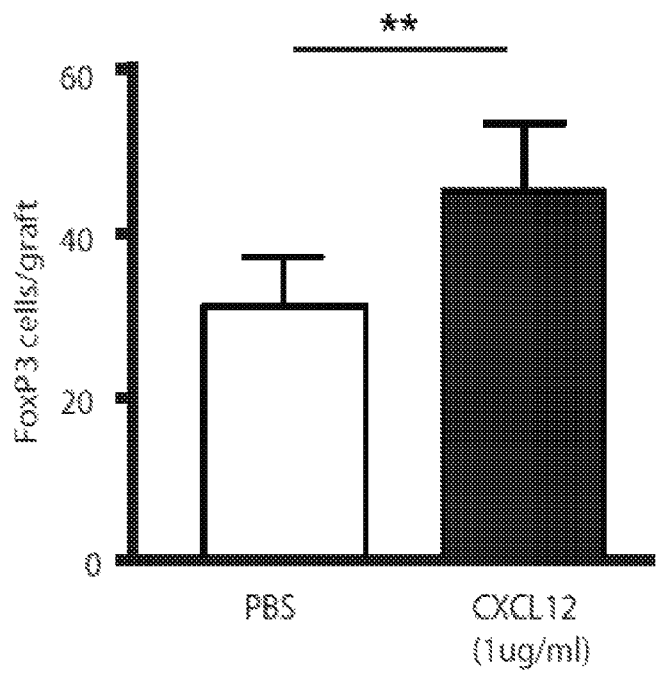

In this Example, it was sought to determine whether coating alloislets with CXCL12 polypeptides prior to transplantation could result in prolonged islet survival and function as well as accumulation of regulatory T cells (Tregs) at the graft site. The islet capsule generally contains fibronectin, and, without wishing to be bound by theory, CXCL12 can both stably bind to and elute from this matrix protein (15). Accordingly, islets from BALB/C mice were exposed to a buffered solution (e.g., PBS) or coated with CXCL12 at a concentration of about 100 ng/ml or about 1 µg/ml and transplanted under the left kidney capsule of streptozotocin (STZ)-treated diabetic C57BL/6 mice. Mice were sacrificed at the point when they returned to a diabetic state with two sequential blood glucose recordings of >250 mg/dl. Allogeneic islet grafts coated with CXCL12 at ~1 µg/ml resulted in the maintenance of recipient mice in a non-diabetic state for a significantly longer time than alloislets that were exposed to PBS alone (p=0.012; Kaplan-Mayer log rank test) (FIG. 1A). Islets coated with 100 ng/ml of CXCL12 polypeptides were rejected at a similar rate to PBS-exposed islets (p=0.31). Mononuclear cell infiltration into the grafts was reduced in the context of CXCL12 coating at about 1 µg/ml compared to PBS controls (FIG. 1B). Insulin expression and CXCL12 presence were also shown in CXCL12-coated alloislets compared to PBS-treated allografts (FIG. 1B). CD3 and FoxP3 T-cell infiltration into grafts was quantified. CD3+ T-cell infiltration into islet grafts was significantly reduced in CXCL12 compared to PBS-exposed alloislets as determined by immunohistochemistry (FIG. 1C, p=0.001). Further, CXCL12 coating of islet allografts was associated with a significant increase in FoxP3+ T-cell infiltration within and around the CXCL12-coated graft compared to PBS-exposed alloislets (FIG. 1D, p=0.0016).

Example 2

Concurrent Use of CXCL12 Coating and Low Dose Cyclosporine A

Figure 2A:
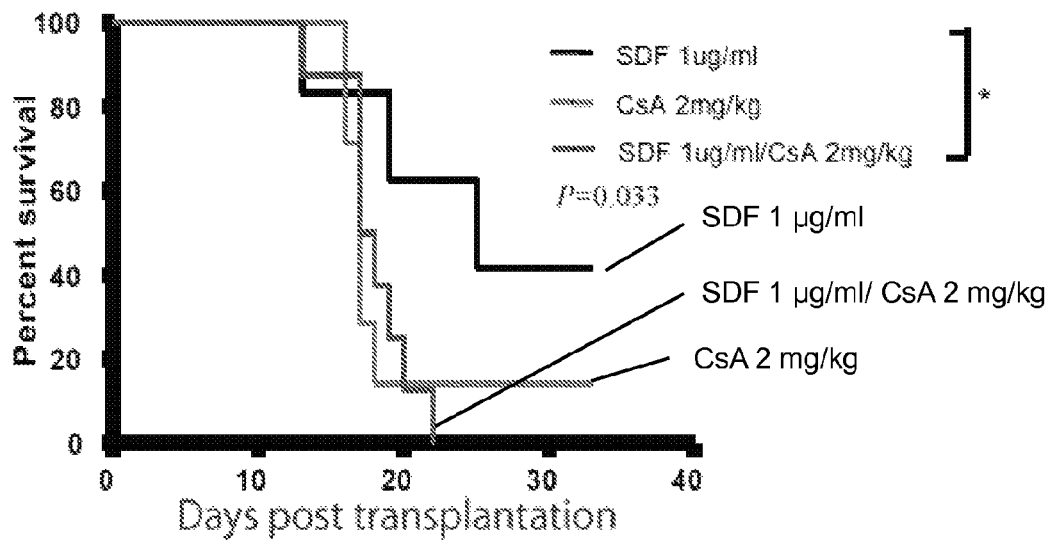
FIGS. 2A-2C show that low dose CsA treatment with CXCL12 coated allogeneic islets does not increase graft survival.
Figure 2B:
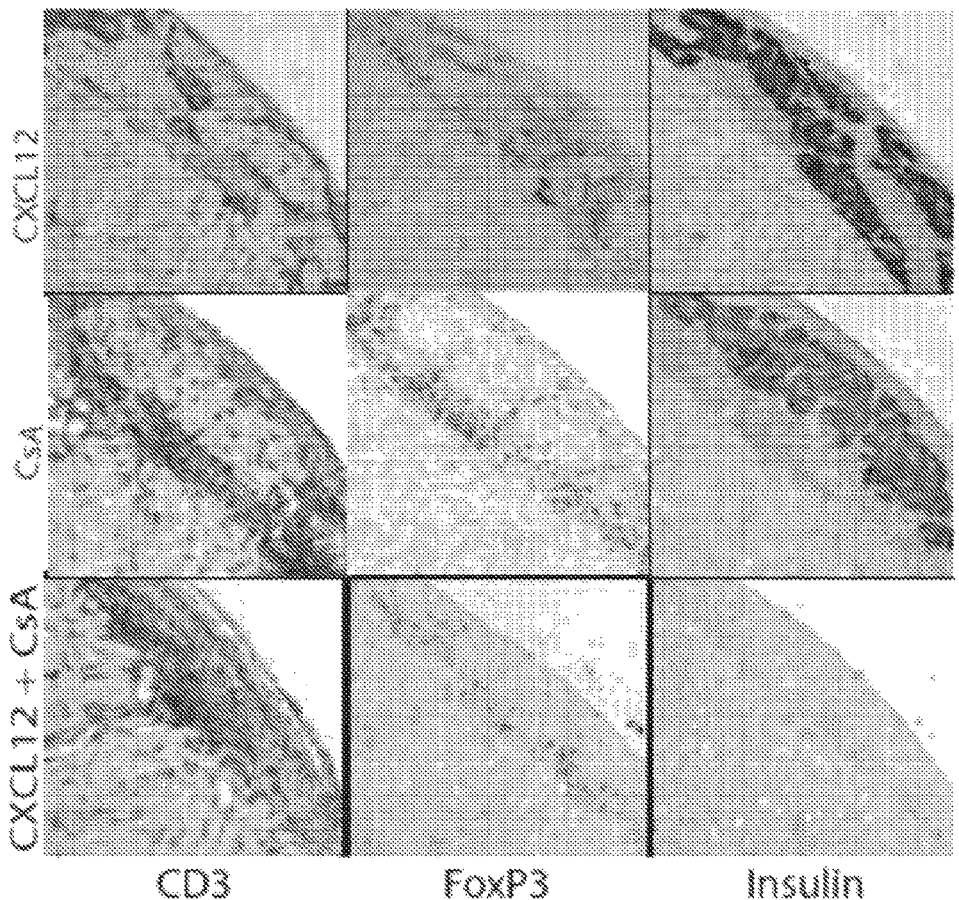
Figure 2C:
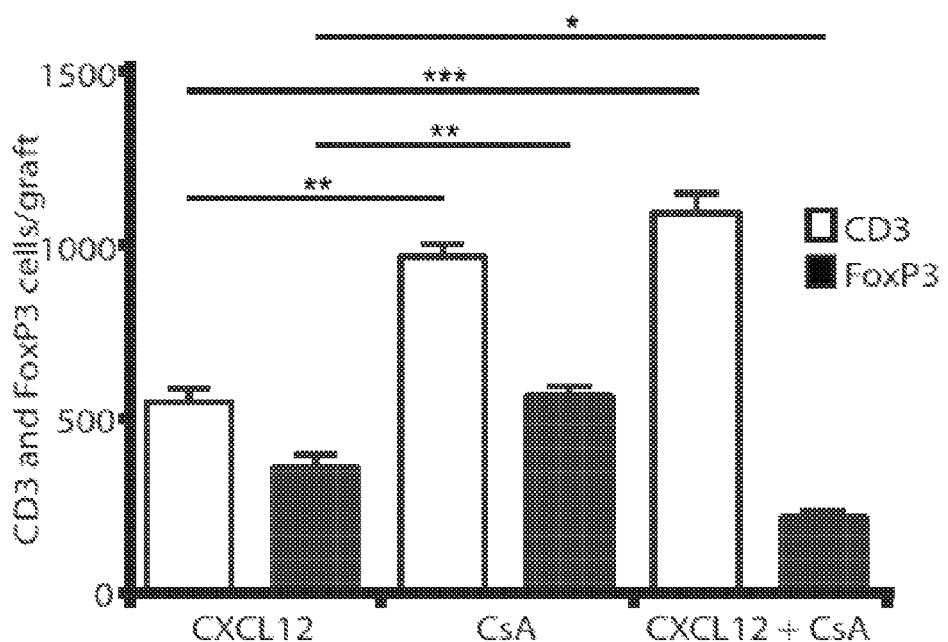

It was next sought to determine whether concurrent use of systemic immunosuppression, for example, in the form of low dose of Cyclosporin A (CsA)(e.g., ~2 mg/kg) treatment, could enhance CXCL12-coated alloislet survival. While CXCL12 coating alone was shown to prolong alloislet survival compared to PBS-exposed controls in these experiments (p=0.0245), CXCL12 coating in combination with low dose CsA treatment did not appear to extend islet survival and the combination of CXCL12 coating and CsA treatment could result in reduced islet survival in comparison to CXCL12 coating alone (p=0.046) (FIG. 2A). Significant differences in islet survival and between control and experimental groups were shown by 23 days post transplantation. Staining of islet grafts showed heavy infiltration of CD3+ T-cells in CXCL12 coating plus CsA treated animals compared to CXCL12 coating alone (p=0.0002) or CsA treated alone (p=0.0027) (FIGS. 2B-2C). The addition of low dose CsA to the treatment of animals receiving CXCL12-coated islets also led to a significant reduction in FoxP3 cell infiltration into the graft compared to CXCL12 coated islets alone (p=0.0188) (FIG. 2C). It was previously discussed that CsA inhibits specific elements of the signaling pathway for CXCL12, and, for example, chemokine-mediated cell migration (16). The findings presented herein indicate that concurrent use of CXCL12 coating and low dose cyclosporine A does not appear to augment an immune protective effect in alloislet transplantation.

Figure 3A:
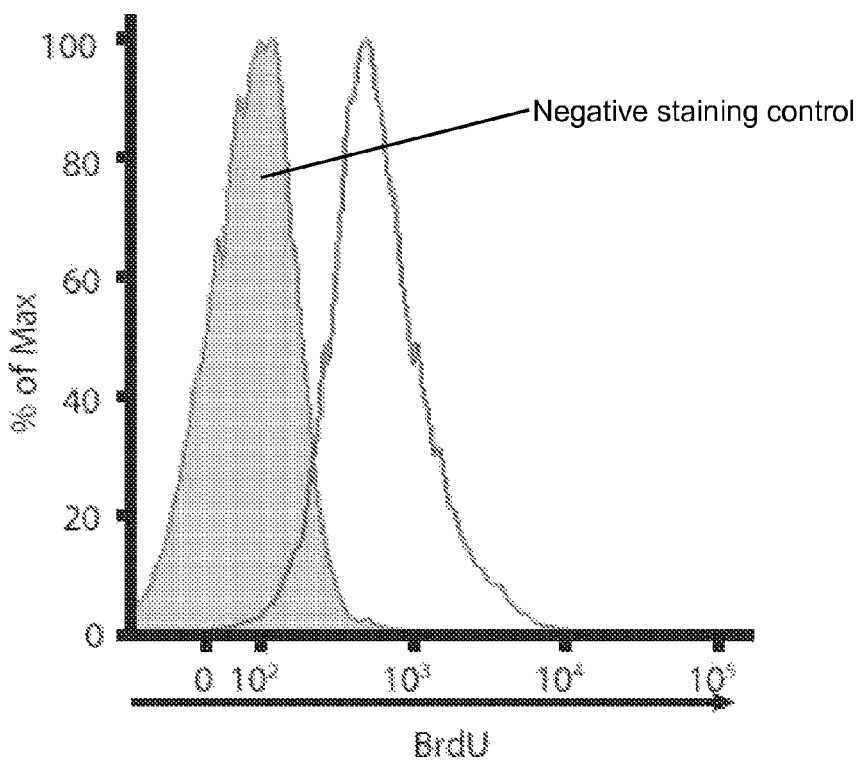
FIGS. 3A-3C show that CXCL12 coating does not affect the number of C57BL/6-specific CD4 T-Cells. Spleens were removed from C57BL/6 mice 10 days post BALB/c islet transplant and splenocytes were stimulated with mitomycin-C treated BALB/c splenocytes in the presence of 1 mM BrdU. Cells were then stained for the incorporation of BrdU.
Figure 3B:
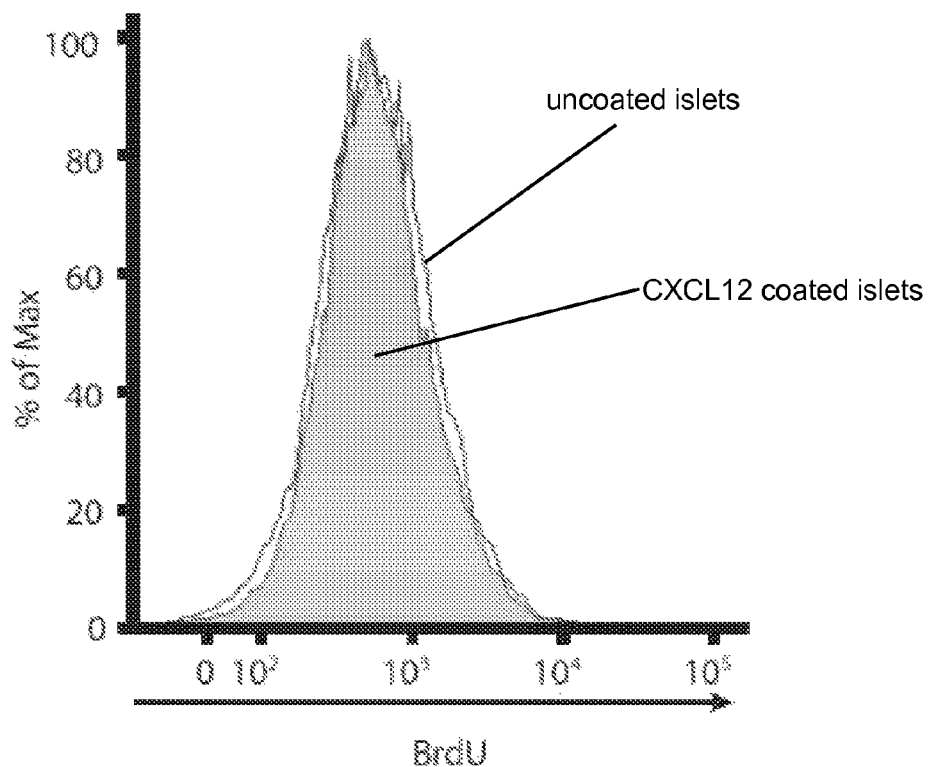
Figure 3C:
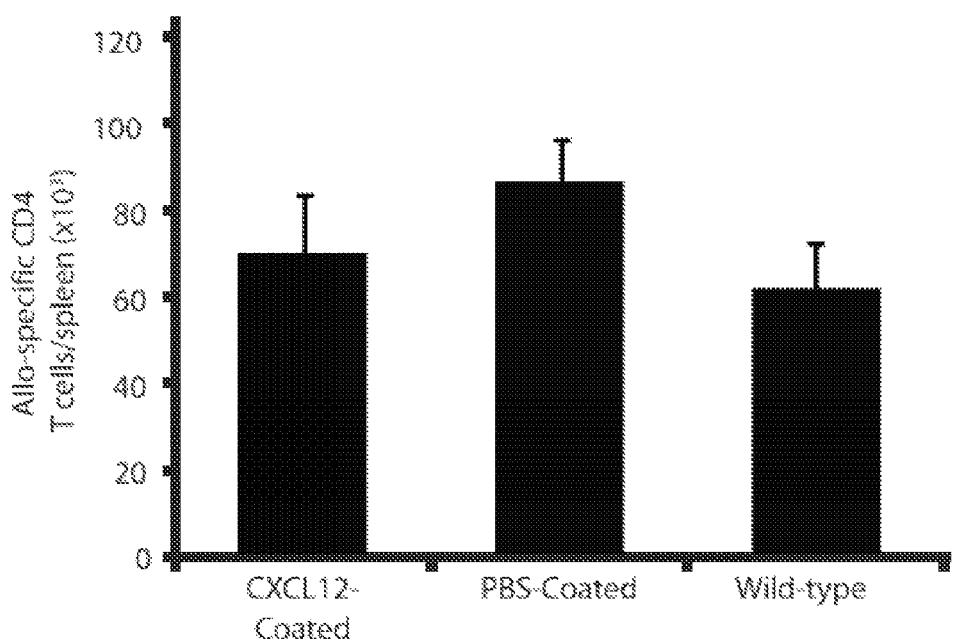

Since the CXCL12-coated islets show a longer survival than PBS-exposed islets, it was next sought to determine whether this phenomenon was due to an effect of the chemokine on cell-mediated anti-islet immunity. To ascertain the level of allo-reactivity, a mixed lymphocyte reaction (MLR) was carried out from mice 21 days after they received either CXCL 12-coated or uncoated islet transplants. No difference was detected between these two groups, indicating that CXCL12 creates an anatomic niche that can slow T-cell-mediated rejection but does not impact the generation of anti-islet immunity (FIGS. 3A-3C). Thus, without wishing to be bound by theory, in some embodiments, CXCL12 coating can induce local immune isolation rather than preventing the generation of systemic anti-allogeneic cell-mediated responses.

Example 3

Figure 4A:
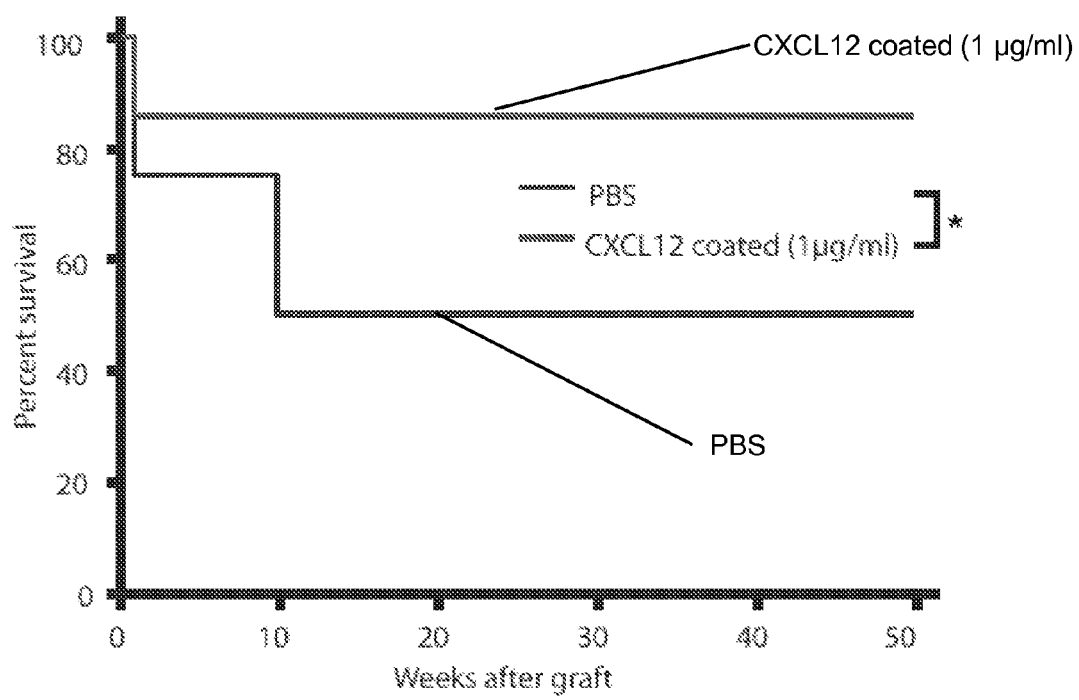
FIGS. 4A-4C show experimental data of CXCL12 coating or PBS exposure of NOD/LtJ mouse syngeneic islets transplanted under the renal capsule of STZ treated diabetic NOD/LtJ mice.
Figure 4B:
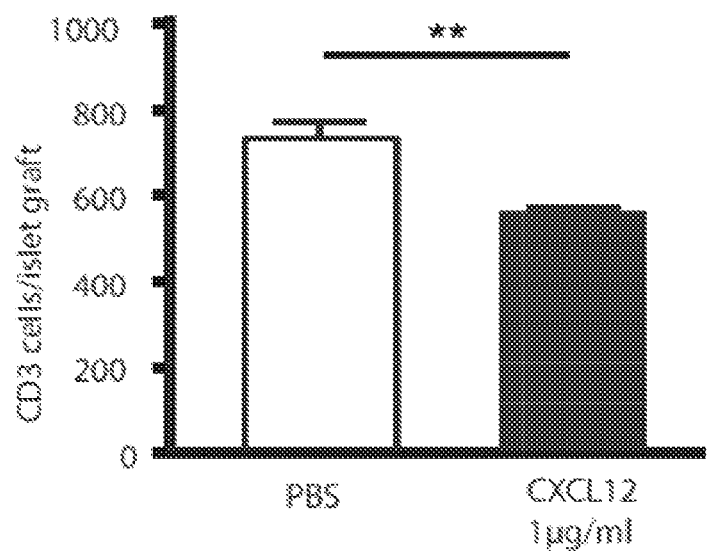
Figure 4C:
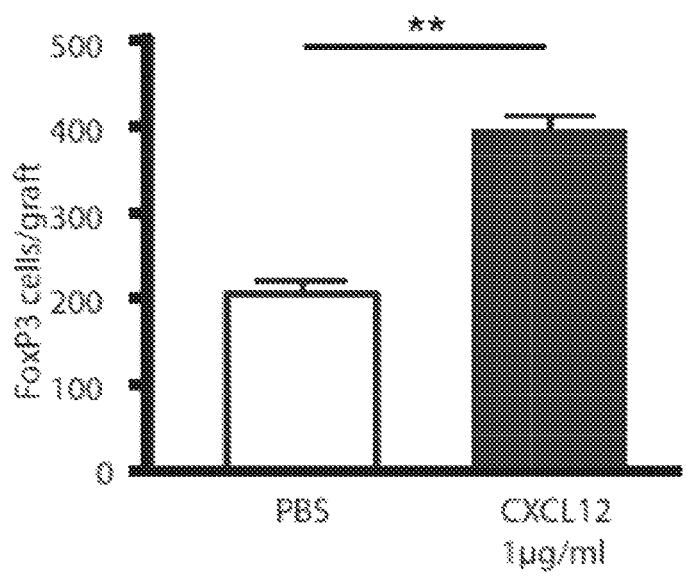
Figure 5A:
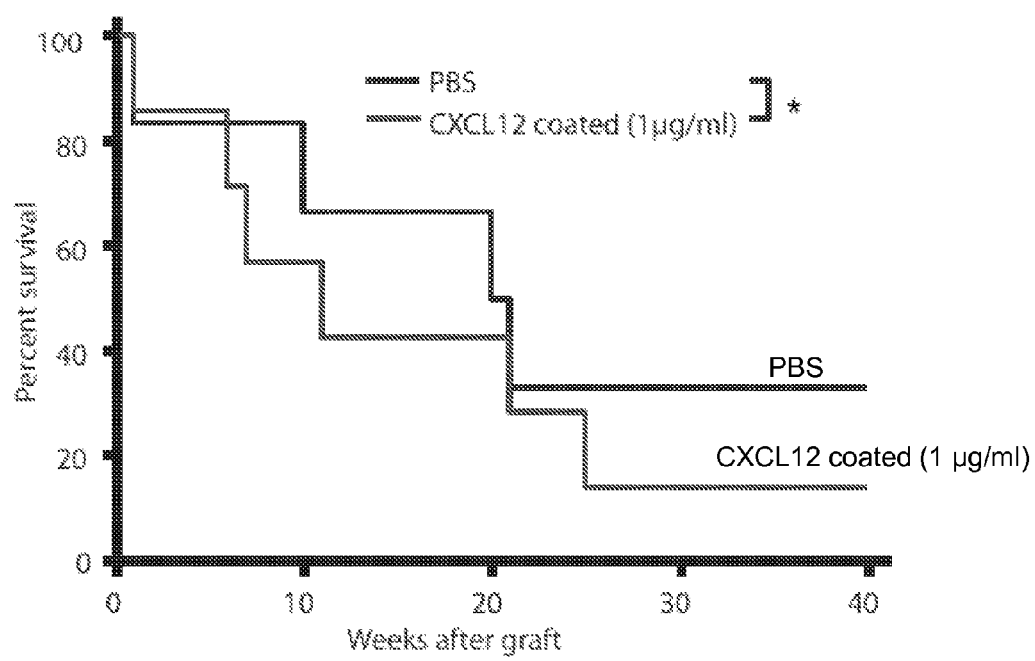
FIGS. 5A-5D show experimental data of CXCL12 coating or PBS exposure of NOD/LtJ mouse syngeneic islets transplanted under the renal capsule of spontaneously diabetic NOD/LtJ mice.
Figure 5B:
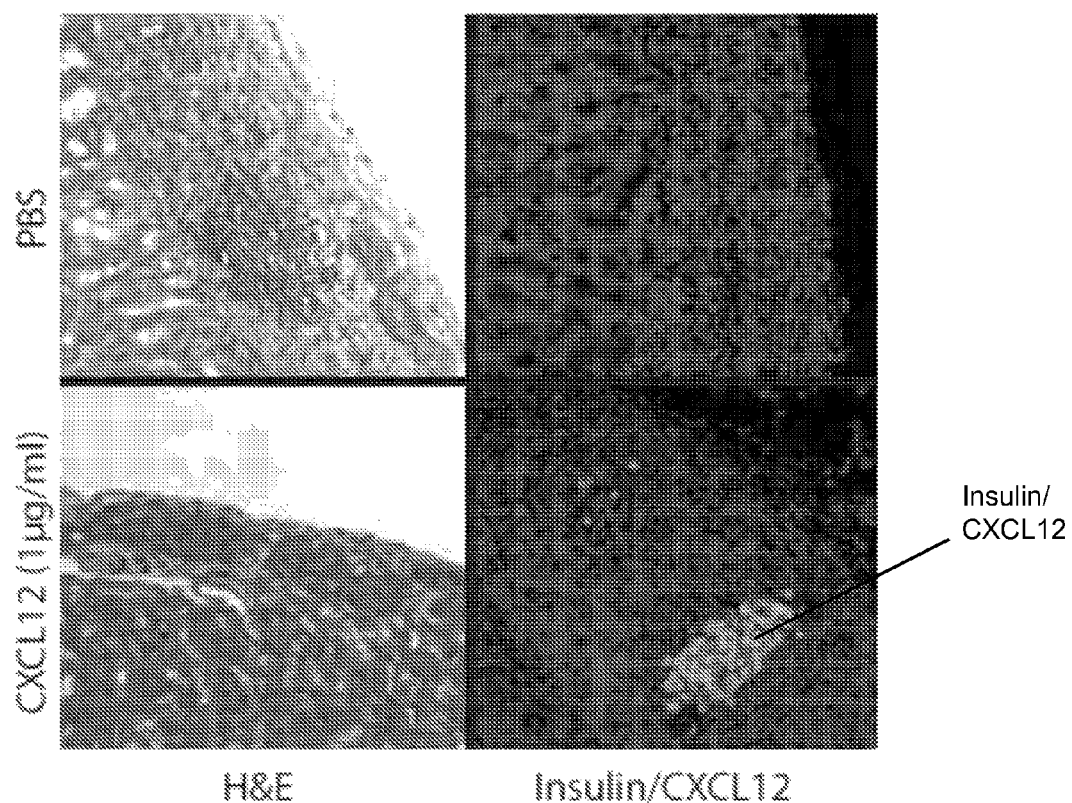
Figure 5C:
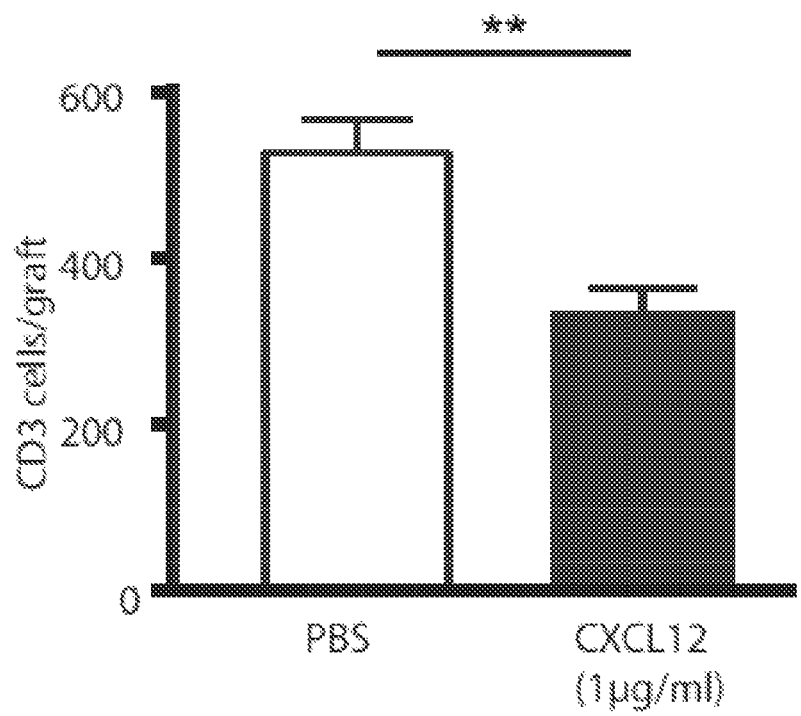
Figure 5D:
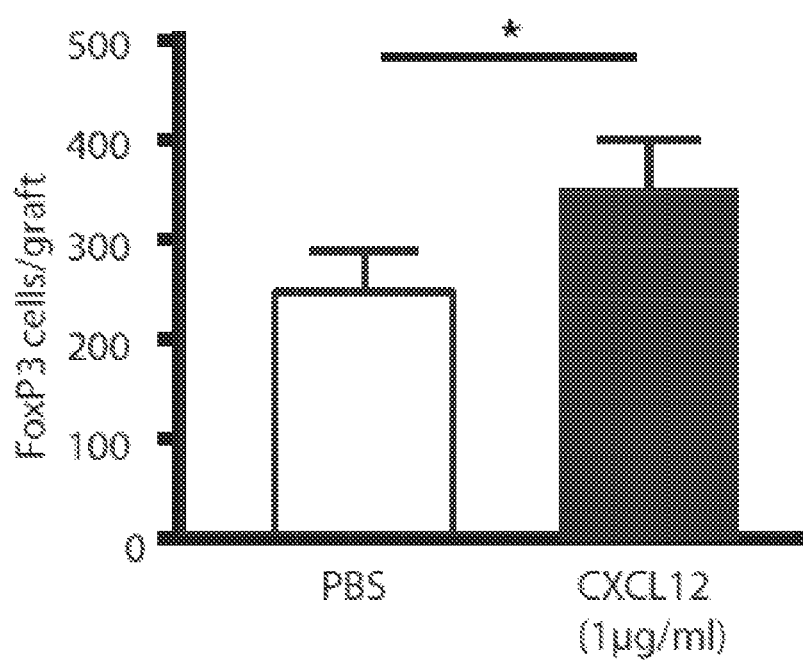

Transplantation of CXCL12-Coated Syngeneic Islets in Prediabetic and Diabetic Mouse Model To determine whether CXCL12 coating could play a role in reducing or preventing rejection in the context of syngeneic islet transplantation, diabetic NOD/LtJ mice was used. In this model, syngeneic islets from non-diabetic NOD/LtJ mice were transplanted into STZ-treated diabetic NOD/LtJ mice. CXCL12 coating of syngeneic islets led to a significantly longer period of normoglycemia than PBS-exposed islets (FIG. 4A) (p=0.017). Histopathological and immunohistochemical studies showed heavy mononuclear cell infiltration into PBS-treated islets but not CXCL12-coated islets (images not shown). That is, H&E staining showed decreased mononuclear cell infiltration into islet grafts coated with ~1 µg/ml CXCL12 and immunofluorescent staining for insulin and CXCL12 showed increased levels of both proteins in CXCL12 coated grafts. Staining for CXCL12 and insulin in this experiment showed healthy insulin-producing and CXCL12-positive islets in comparison to PBS-exposed islets. CXCL12 coating of syngeneic islets also reduced CD3+ T-cell infiltration into donor islets compared to PBS-exposed syngeneic NOD/LtJ islets (FIG. 4B, p=0.0081). CXCL12 coating of syngeneic NOD/LtJ islets also led to a significantly increased number of FoxP3+ cells in the islet graft site compared to PBS-treated controls (p=0.0019) (FIG. 4C). While CXCL12 coating of syngeneic islets did not appear to reduce the rate of recurrence of diabetes in spontaneously diabetic NOD/LtJ mice (FIG. 5A) (p=0.24), hematoxylin and eosin and insulin/CXCL12 staining showed reduced mononuclear cell infiltration and increased insulin expression in CXCL12-coated islets compared to controls (FIGS. 5B-5C). In addition, there was a consistent reduction in CD3+ T-cell infiltration and increased FoxP3+ cell infiltration into the CXCL12-coated graft compared to PBS controls (FIG. 5D). Taken together, CXCL12 coating of syngeneic islets can prevent rejection in a prediabetic model but not necessarily in a diabetic model. This lack of a pro-survival effect of CXCL12 coating in this syngeneic transplant setting can be attributable to, e.g., inefficiency of blocking established humoral anti-islet immune responses by a CXCL12 coating of transplanted islets.

Example 4

Use of Alginate Encapsulant (Islet Cells Encapsulated in Alginate) Incorporating CXCL12 in Sensitized and Non Sensitized Recipients It was previously discussed that early expression of insulin autoantibodies correlates with progression to diabetes and probably primarily reflects insulitis (17-19). As shown in Example 3, the efficacy of CXCL12 coating of islets for transplantation was more effective as an intervention in the setting of pre-formed anti-islet antibodies. In this Example, it was sought to determine if incorporation of CXCL12 into alginate microcapsules could protect transplanted islets by providing both a physical and a biological barrier to cell-mediated and humoral anti-islet immunity.

Figure 6A:
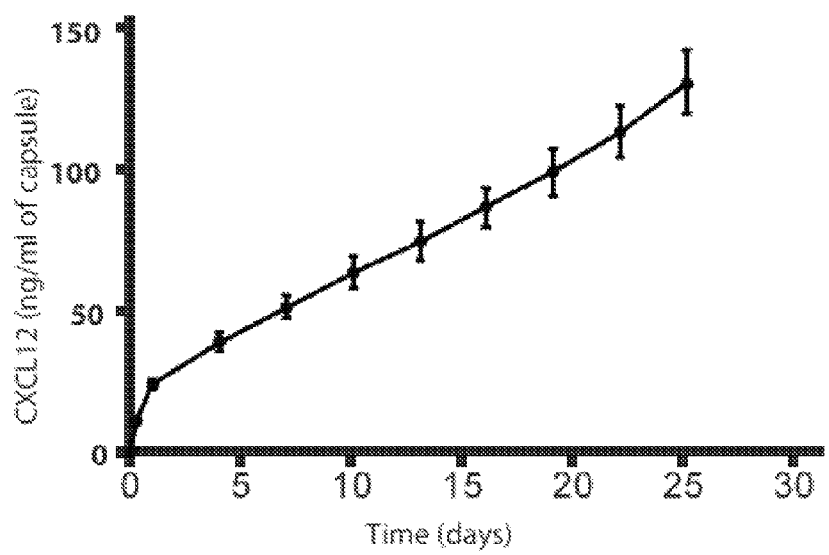
FIGS. 6A-6F show that incorporation of CXCL12 into Ca-LVM alginate capsules delays rejection of allogeneic and xenogeneic islets transplanted into the peritoneal cavity.
Figure 6B:
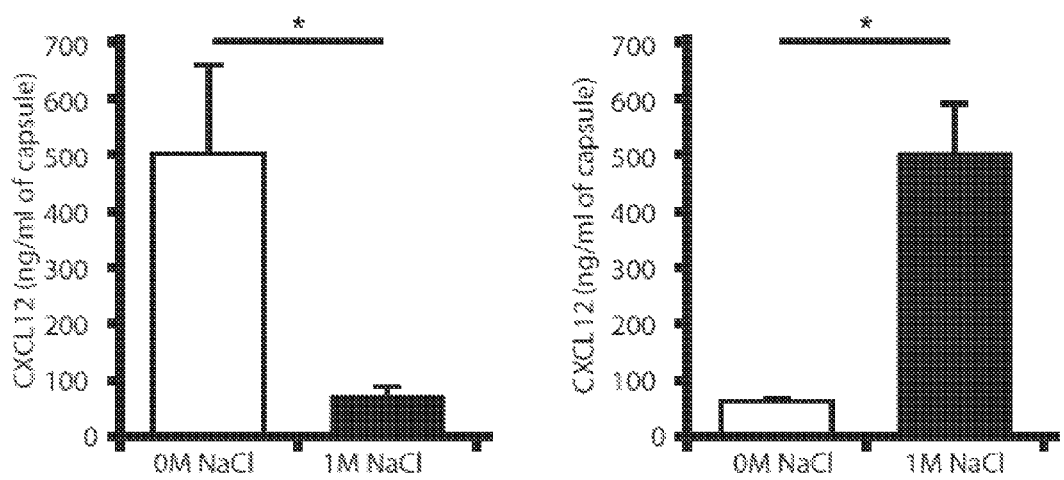
Figure 6C:
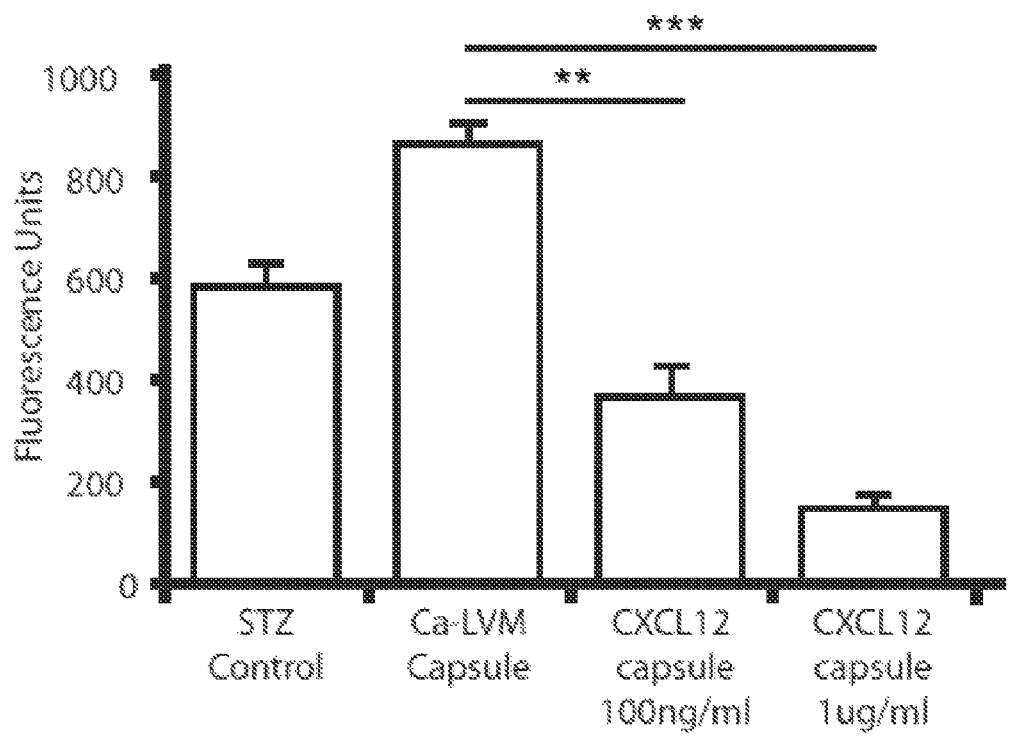

In one embodiment, the encapsulation matrix comprised of 2% low viscosity, high mannuronic acid, calcium crosslinked alginate (Ca-LVM) and CXCL12 polypeptides incorporated therein (referred to as "Ca-LVM-CXCL12" hereafter). FIG. 6A shows that Ca-LVM-CXCL12 encapsulants resulted in prolonged release of CXCL12 in vitro at about 1.75+/−0.4 ng/ml/hr after an initial rapid release over the first 3 hours. There was also prolonged retention of CXCL12 in the alginate matrix, resulting in residual intracapsular CXCL12 concentration between 100 and 200 ng/ml after 22 days of in vitro incubation of cell-free capsules (data not shown). Without wishing to be bound by theory, the prolonged retention of CXCL12 in the matrix was likely due to electrostatic interactions between the positively charged chemokine (pI of 9) and the negatively charged alginate (pI of 2) (20) This was supported by the observation that CXCL12 was effectively eluted into the medium as a result of incubation with 1M NaCl in comparison to medium containing no NaCl. Similarly, CXCL12 was retained within the capsule when incubated in the absence of NaCl but was extracted from the capsule in 1M NaCl. (FIG. 6B). As CXCL12 has also been shown to be a pro-survival factor for islets, the effect of the incorporation of CXCL12 into a Ca-LVM encapsulant on islet viability was also evaluated. The findings presented herein show that incorporation of CXCL12 into the encapsulant significantly decreased the level of caspase-3 activity in encapsulated islets determined at least after 48 hours of in vitro culture as compared to unmodified Ca-LVM alginate (100 ng/ml CXCL12; p=0.0019)(1 µg/ml CXCXL12; p=0.00028) (FIG. 6C).

Figure 6D:
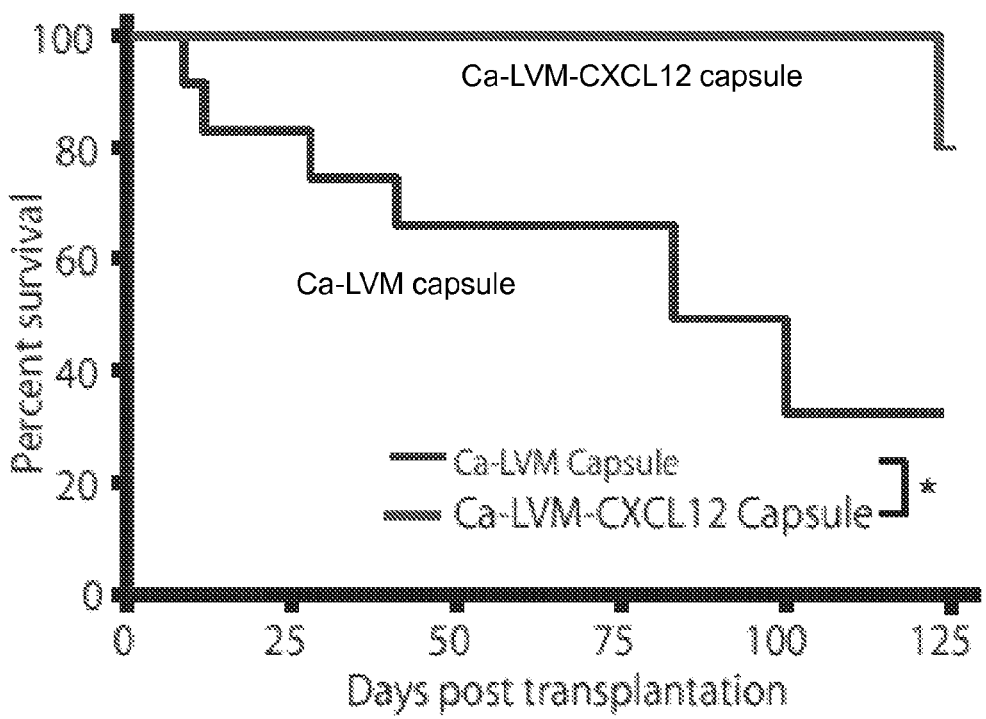
Figure 6E:
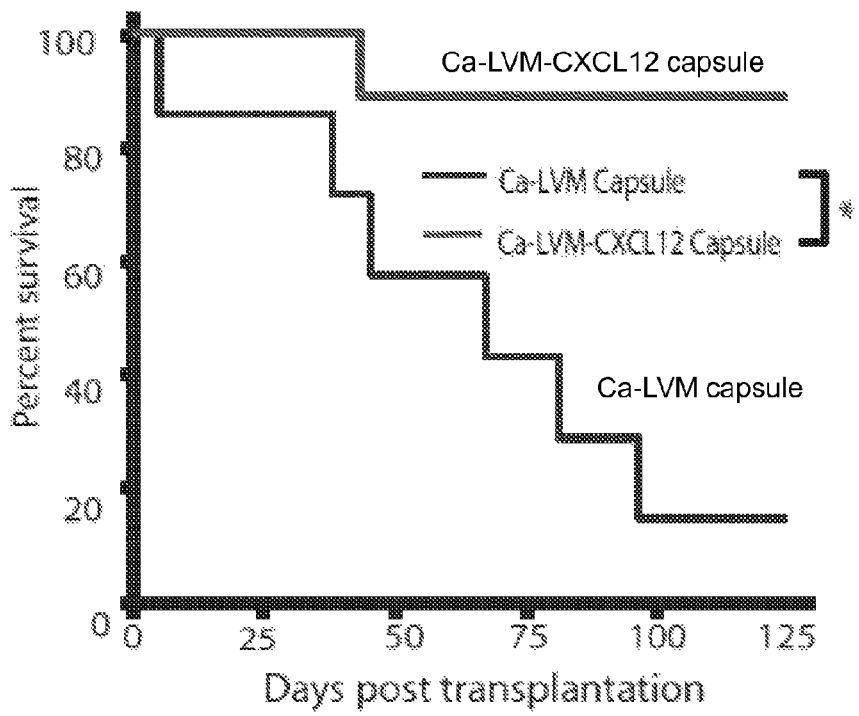

Alloislet transplantation of Ca-LVM-CXCL12 encapsulants into spontaneously diabetic NOD/LtJ mice without systemic immune suppression was evaluated. When alloislets were transplanted into the peritoneal cavity of diabetic NOD/LtJ mice, incorporation of CXCL12 into the Ca-LVM alginate significantly prolonged islet function and survival as compared to the unmodified Ca-LVM alginate (Mean days in non diabetic state post-transplantation—Ca-LVM-CXCL12=136; Ca-LVM=62) (p=0.048) (FIG. 6D). Histopathological studies of retrieved Ca-LVM-CXCL12 capsules at 12 weeks post-transplant showed intact islet morphology in comparison to unmodified Ca-LVM capsules in which islets were necrotic or degenerative (Data not shown). Islets encapsulated with Ca-LVM-CXCL12 appeared viable and intact using phase contrast microscopy and H&E staining at 6 weeks post-transplantation in comparison to necrotic islets encapsulated in unmodified Ca-LVM. Accordingly, CXCL12 incorporation improves islet health and decreases necrosis six weeks after transplant. Alloislets from C57BL/6 mice were then transplanted into spontaneously diabetic NOD/LtJ mice that had previously received and rejected a skin transplant from C57/B6 mice. Alloislets encapsulated with Ca-LVM-CXCL12 survived and maintained a normoglycemic state significantly longer in recipients than islets encapsulated with Ca-LVM alone (FIG. 6E). This shows that CXCL12 incorporation into encapsulant protected islets from an immune memory response in recipient mice.

Figure 6F:
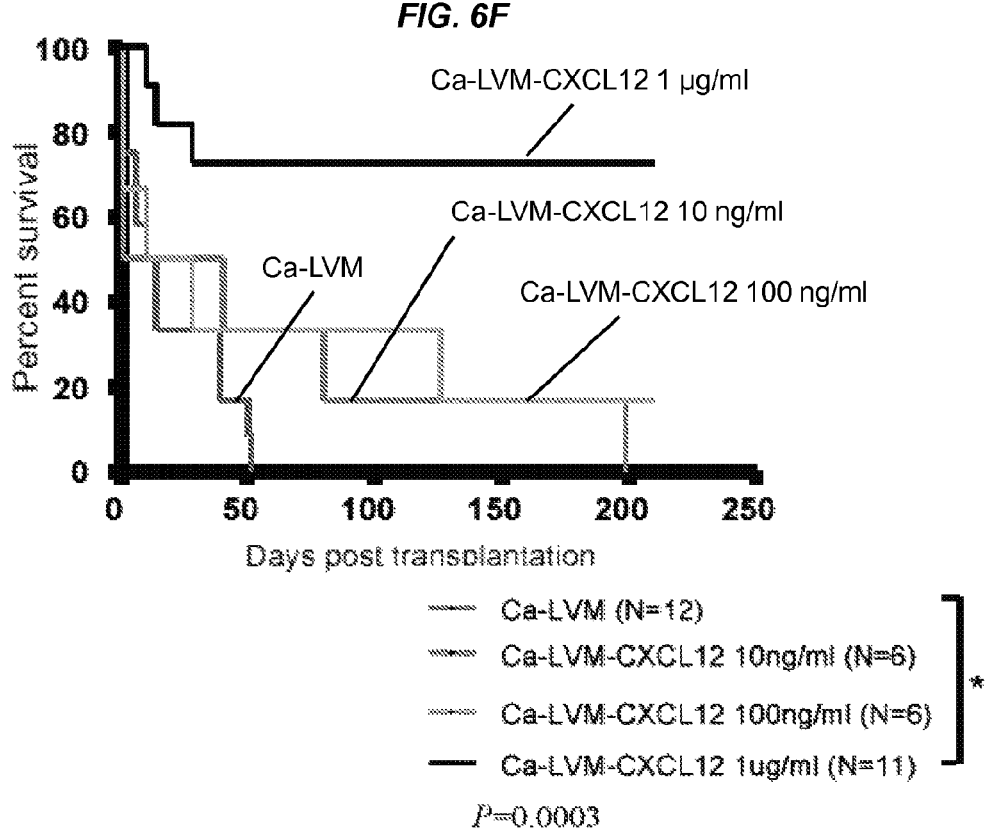

It was then sought to determine whether xenoislets could be protected by an alginate encapsulant that incorporated CXCL12. Porcine xenoislets were encapsulated in Ca-LVM or Ca-LVM with CXCL12 at a concentration of about 10 ng/ml, about 100 ng/ml or about 1 µg/ml, and transplanted into the peritoneal cavity of diabetic C57BL/6 mice. Porcine islets encapsulated with Ca-LVM containing CXCL12 at a concentration of about 1 µg/ml sustained normoglycemia in recipient mice for a significantly longer period of time than either Ca-LVM or Ca-LVM-CXCL12 (~10 ng/ml) encapsulated islets (FIG. 6F).

Example 5

Figure 7A:
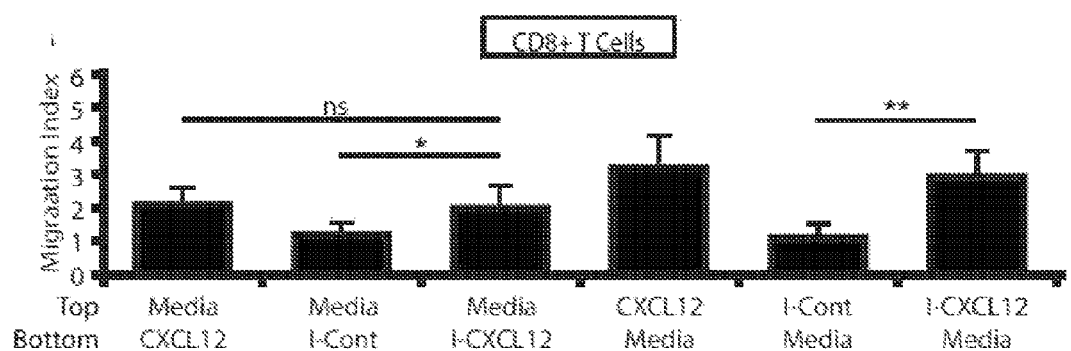
FIGS. 7A-7G show migratory behaviors of T-cell subpopulations to CXCL12 and associated CXCR4 expression.
Figure 7B:
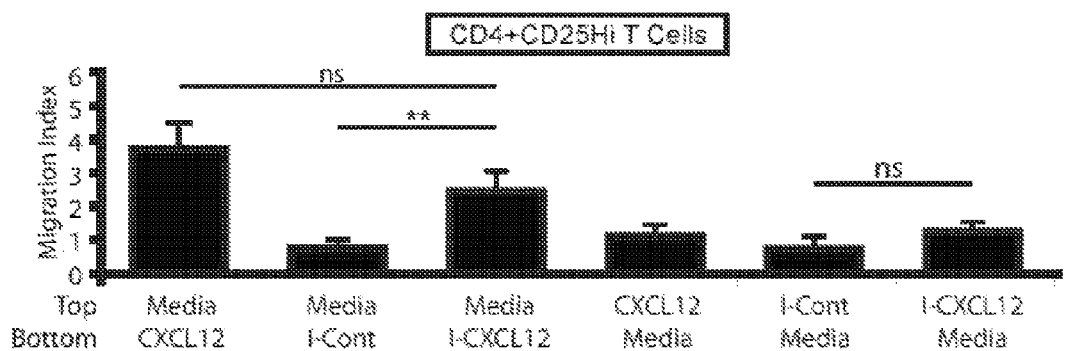
Figure 7C:
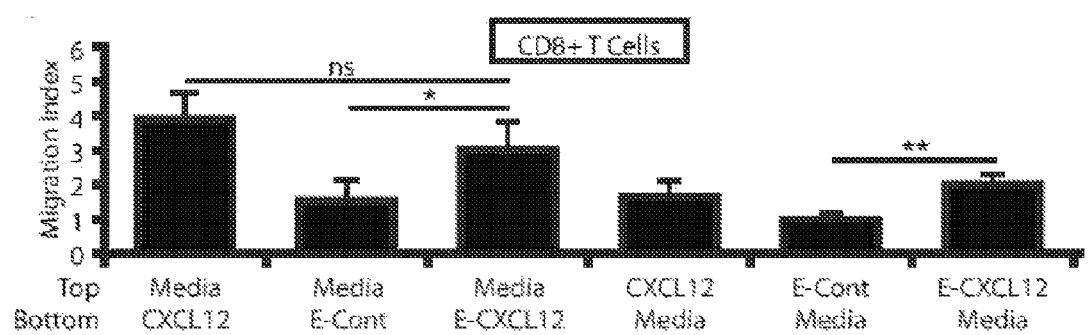
Figure 7D:
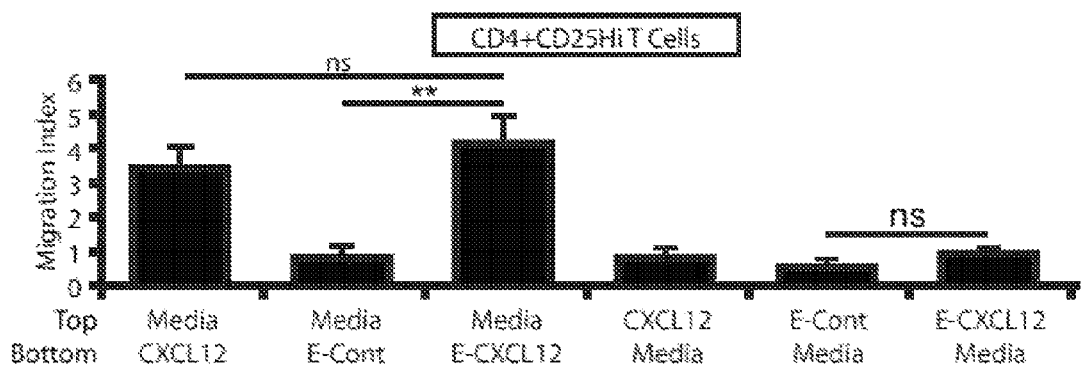

Effect of CXCL12 Coating or Microencapsulation on CD8+ T-Cells and Treg Cells In Vitro In order to determine whether the mechanism by which CXCL12 coating or incorporation in the encapsulant sustains immune isolation of the xeno or alloislet graft involves selective repulsion of CD8+ T-cells and attraction of CD4+ Treg cells to the graft site, the expression of CXCR4 on and migration of T-cell subpopulations from NOD/LtJ mice were studied by flow cytometry and transmigration assays, respectively. T-cells derived from NOD/LtJ mice in response to medium alone, recombinant CXCL12, CXCL12-coated or Ca-LVM-CXL12 encapsulated islets were studied in Boyden chamber based assays. Upper chambers were loaded with purified CD3+CD8+ T cells (FIGS. 7A and 7C) or CD4+CD25hi+ Treg cells (FIGS. 7B and 7D) for each condition. Upper and lower wells were loaded with media, CXCL12 (~1 µg/ml) or islets coated with CXCL12 (~1 µg/ml) or encapsulated with Ca-LVM-CXCL12 (~1 µg/ml). Both CD3+CD8+ T-cells and CD4+CD25Hi Tregs underwent chemotaxis in response to CXCL12, CXCL12-coated or Ca-LVM-CXCL12-encapsulated islets. However, a significantly larger fugetactic response was detected when CD8+ cells were incubated with CXCL12, CXCL12-coated islets or Ca-LVM-CXCL12-encapsulated islets than Treg cells. No detectable levels of Treg cell fugetaxis were measured in the conditions performed.

Figure 7E:
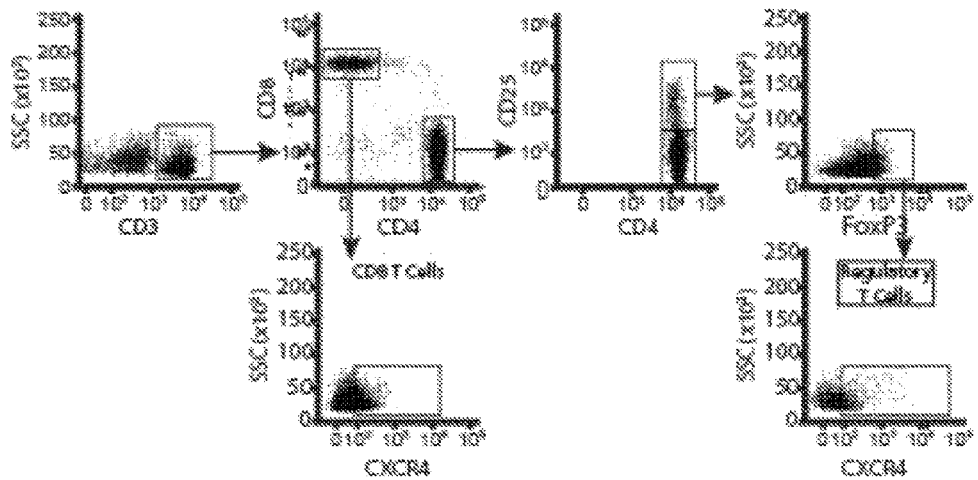
Figure 7F:
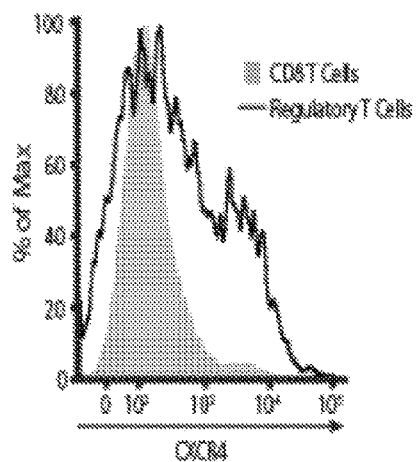
Figure 7G:
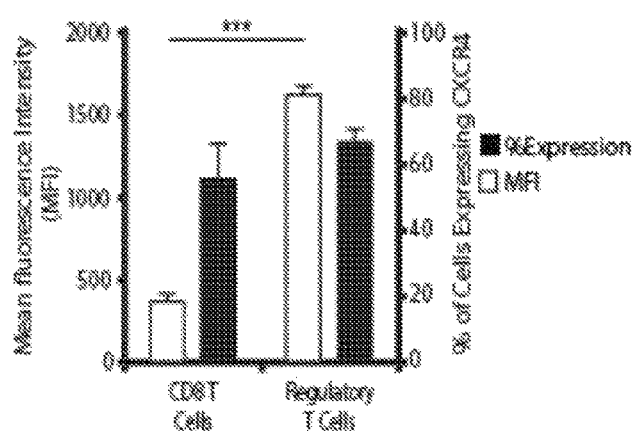
Figure 8:
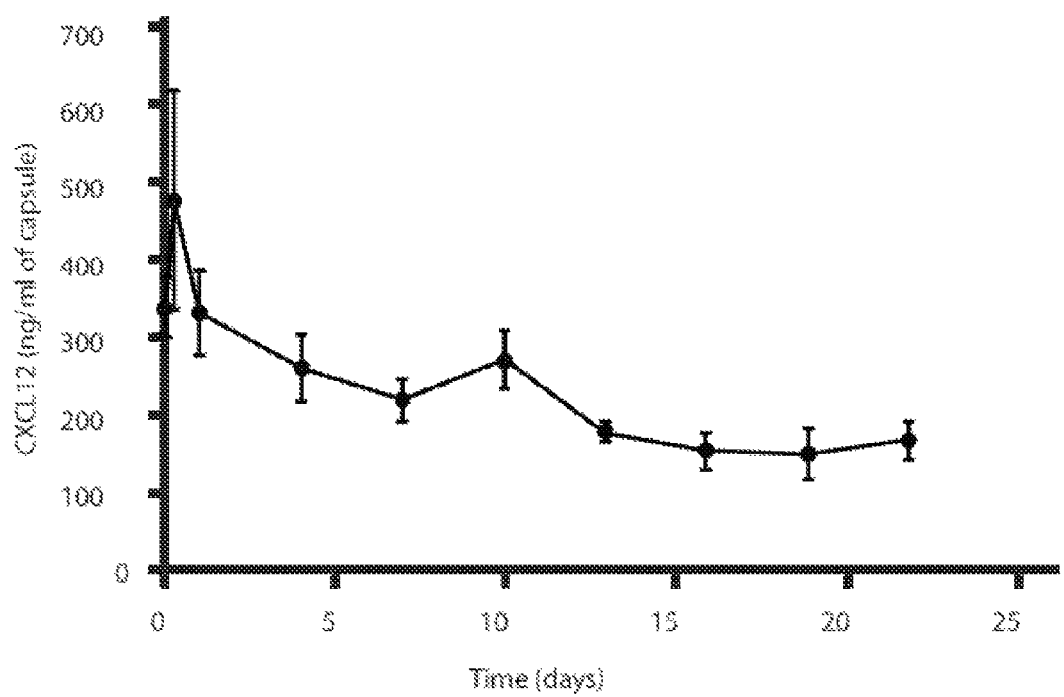
FIG. 8 is a line graph showing kinetics of CXCL12 retention within calcium cross-linked 3.3% alginate encapsulant over time in vitro. The concentration of CXCL12 in un-cross-linked sodium alginate was 1 µg/ml (n=3). There were no differences in CXCL12 release profiles for alginate concentrations of 1.5% to 3.3% (data not shown).

It was next sought to determine whether the differential migratory responses to CXCL12 between CD8+ T cells and CD4+ Treg cells could be, in part, due to the differential expression of the chemokine's cognate receptor, CXCR4 on these two T-cell subpopulations. CD8+ T-cells from the spleen of NOD/LtJ mice expressed significantly lower levels of CXCR4 than CD4+CD25HiFoxP3+ Treg cells (p<0.005) (FIGS. 7E and 7F). These data show that CXCL12 coating or CXCL12 incorporation in an encapsulant surrounding transplanted alloislets can result in preferential recruitment of Treg cells within the graft while repelling CD8+ T-cells in this transplant model.

Discussion

The findings presented in Examples 1-5 show that that coating of islets with CXCL12 can lead to a delay in islet rejection in allo and in syngeneic islet transplantation in STZ treated diabetic NOD/LtJ mice. Specifically, it was observed that a Ca-LVM based alginate encapsulant incorporating CXCL12 protected alloislets with both pre-existent humoral and cell mediated anti-islet responses in the context of transplantation into diabetic and sensitized NOD/LtJ mice.

The transplant models in Examples 1-5 show that coating or encapsulation of islets with CXCL12 results in accumulation of Treg cells at the graft site.

Accordingly, without wishing to be bound by theory, in both tumor and transplant settings the retention/accumulation of Treg cells can be be associated with the establishment of an immune suppressive microenvironment. The findings presented herein show that coating or encapsulation of allo or xenoislets with CXCL12 can lead to delayed islet rejection and concomitant prolonged islet function through the induction of local immune isolation. The discovery that CXCL12 incorporation into clinical grade alginate encapsulant surrounding transplanted allo and xenoislets allows sustained islet function and protection from immune destruction in the sensitized host without systemic immune suppression is a surprising and also clinically translatable finding.

Exemplary Materials and Methods Used in Examples 1-5

Animals and induction of diabetes. Six-week-old female BALB/c ($H2^d$), 6-week-old female C57BL/6 ($H2^b$), and 6-8 week old female NOD/LtJ ($H2^{g7}$) mice were used. Animals can be purchased, e.g., from Jackson Laboratory (Bar Harbor, Me.). All procedures were carried out following the Public Health Service Policy on Humane Care of Laboratory Animals and approved by the Subcommittee on Research Animal Care at Massachusetts General Hospital. Hyperglycemia was spontaneous in 18-20-week-old NOD/LtJ mice and was induced in 4- and 6-week-old NOD/LtJ and 6-week-old C57BL/6 mice by intraperitoneal (IP) injection of 200 mg/kg streptozotocin (Sigma-Aldrich, St. Louis, Mo.). Mice with three consecutive blood glucose readings above 250 mg/dl were considered hyperglycemic.

Pancreatic islet isolation, CXCL12 coating and incorporation of the chemokine into alginate encapsulant. Primary islets were isolated from donor mice as previously described in Papeta et al., Transplantation 83, 174 (2007). For example, islets were isolated from female 6-week-old BALB/c donors, female 6-week-old C57BL/6 donors, or female 4-week-old NOD/LtJ donors. Pancreata were infused via the common bile duct with Liberase TL (e.g., ~83 μg/ml) (Roche Diagnostics, Indianapolis, Ind.) and digested for ~20 minutes at ~37° C. Islets were purified on a polysucrose/glucose density gradient (Mediatech, Manassas, Va.) and selected under a microscope. The islets were cultured in RPMI 1640 (Mediatech, supplemented with 10% fetal bovine serum, 1% Penicillin/Streptomycin, and 1% L-Glutamine) for at least 2 days or longer to allow for recovery. A minimum of 450 islets to be transplanted via the kidney capsule were incubated at ~37° C. for ~3 hours prior to transplantation in DPBS (Mediatech) with or without ~100 ng/ml or ~1 μg/ml CXCL12 (PeproTech Inc, Rocky Hill, N.J.). Separately, prior to encapsulation, CXCL12 was incorporated into liquid Na-LVM alginate (ultra-pure LVM, Novamatrix) at a concentration of ~1 μg/ml.

Production and transplantation of Ca-LVM alginate capsules. Approximately 1000 C57BL/6 islets were mixed in ~0.75 mL of ~1.5% alginate (ultra-pure LVM, Novamatrix, Drammen, Norway)) in ~300 mOsmo NaCl solution with or without ~1 μg/ml CXCL12. The mixture was then run through a syringe driven encapsulator (Inotech Research Encapsulator, IE-50R) using a 300 μm nozzle charged to 1.21 kV vibrating at 1500 Hz. Alginate was cross-linked, e.g., in 300 mOsmo (approximately 118 mM) $CaCl_2$, for about 5 minutes, filtered, and washed with DMEM (Mediatech) to remove excess calcium.

CXCL12 retention and release from alginate capsules and caspase-3 assay. Prior to capsule formation, ~3.6% LVM was mixed with ~10 μg/mL CXCL12 (Peprotech, Rocky Hill, N.J.) stock solution to yield ~3.3% LVM with ~1 μg/mL CXCL12. Calcium cross-linked LVM capsules were formed using an electrostatic droplet generator (Nisco Engineering, Zurich, Switzerland), at a charge of 5 kV, using a 0.5 mm nozzle and a flow rate of 30 mL/h. The CXCL12-containing acellular capsules were incubated in non tissue culture treated multi-well plates in DMEM (Sigma Aldrich, St. Louis, Mo.) with ~1.6 g/L bovine serum albumin (Sigma Aldrich). The ratio of capsules to medium was maintained at about 1:2 v/v throughout the course of the experiment. At each time point, a ~0.1 mL sample of capsules was removed and solubilized using a 110 mM sodium citrate solution. Additionally, at each time point, all medium was removed and fresh medium was added. Both medium and solubilized capsule samples were assayed for CXCL12 content by ELISA (R&D Systems, Minneapolis, Minn.). In order to determine the effect of encapsulation in combination with CXCL12 on islet apoptosis, murine islets were encapsulated with alginate encapsulant as described herein with or without ~1 μg/ml CXCL12. As a control, islets can also be exposed to streptozotocin, a known inducer of islet apoptosis. For example, islets can be cultured in this condition in vitro for 48 hours and Caspase-3 activity in encapsulated islets determined using an ELISA based assay (R and D systems, Minneapolis, Minn.).

CXCL12 salting out from alginate capsules. CXCL12 capsules were formed as described above with the following modification; capsules were cross-linked using 20 mM calcium chloride to prevent their dissolution in a high concentration sodium chloride solution. Capsules were incubated in ~1M NaCl with ~0.1% BSA for ~6 hours, after which the solution was collected and the beads were solubilized using 200 mM ethylenediaminetetraacetic acid disodium salt (ED2SS), pH 9.0. The solution and solubilized capsule samples were assayed for CXCL12 content by ELISA, as described above. Control capsules were incubated in NaCL free $CaCl_2$ solution and CXCL12 retained and released from the capsules determined.

Islet transplantation models. Variably treated islets were transplanted under the left renal capsule of recipient mice or were encapsulated in Ca-LVM alginate and were transplanted via the peritoneal cavity. Four different exemplary transplant models were used: (1) BALB/C islets were transplanted under the renal capsule of STZ-induced diabetic C57BL/6 mice; (2) Pre-diabetic (pre-sensitized) NOD/LtJ islets were transplanted under the renal capsule of spontaneously diabetic NOD/LtJ mice; (3) Pre-diabetic (pre-sensitized) NOD/LtJ islets were transplanted under the renal capsule of 6-week-old diabetic (pre-sensitized, STZ-induced diabetic) NOD/LtJ mice; and (4) C57BL/6 islets were encapsulated in Ca-LVM alginate and transplanted into the peritoneal cavity of 6 week old STZ-induced diabetic NOD/LtJ mice.

Monitoring recipients' glycemic control. Recipients' tail vein blood glucose level was monitored at least twice a week and was used to interpret islet graft function. Graft rejection was defined as a return to hyperglycemia (e.g., characterized by three consecutive measurements above 250 mg/dl). Mice were sacrificed upon graft rejection.

Immunohistochemistry and immunofluorescence staining. Kidneys containing sub-capsular islet grafts were fixed in 4% formaldehyde, embedded in paraffin, and 5 μm sections of grafts were cut for slides. Some sections were stained with hematoxylin and eosin (H&E). Immunohistochemistry was also performed using primary antibodies for CD3 (Dako, Denmark), FoxP3 (eBioscience, CA), and insulin (Dako, Denmark). An appropriate secondary antibody was then paired to each primary antibody and DAB (3,3'-Diaminobenzidine) was used as a substrate for the staining. Nuclear staining (blue) was performed with Meyer's haemalum for the avidin-biotin complex IHC staining method. Camera images were taken with a Zeiss Axio Observer Z1 at 10× magnification and islet graft sections were manually scored for $CD3^+$ and/or $FoxP3^+$ T-cell infiltration. The numbers of cells positive for each marker were recorded in 5 randomly selected high-power fields near the graft site. Immunofluorescent staining was also performed using fluorescent primary antibodies for insulin (guinea pig anti-insulin, 1:800, Invitrogen) and CXCL12 (rabbit anti-mouse CXCL12, 1:200, Cell Sciences). Slides were washed, incubated with the primary antibodies overnight at 4° C. and then incubated with the appropriate secondary antibodies for one hour at room temperature (goat anti-guinea pig IgG [Dylight 488, 1:200, Jackson Immunoresearch] and goat anti-rabbit IgG [Dylight 549, 1:200, Jackson Immunoresearch]). Following secondary antibody application, tissues were washed, counter stained with To-Pro-3 (1:5000, Invitrogen), and mounted. Digital images of immunofluorescence slides were obtained by means of confocal microscopy (LSM 5 Pascal, Carl Zeiss).

Cyclosporin a treatment. Diabetic C57BL/6 mice were transplanted with 450 BALB/c islets coated with PBS or CXCL12 (~1 µg/ml). Recipients were treated with one of three treatment groups: (A) Cyclosporin A (CsA, Sigma) injection for recipients of PB S-coated islets; (B) CsA injection for recipients of CXCL12-coated islets; and (C) PBS injection for recipients of CXCL12-coated islets. For groups A and B, CsA was prepared by dissolving in ethanol and injected subcutaneously at ~2 mg/kg on the day of transplantation and daily, thereafter, until graft rejection.

Mixed lymphocyte reaction. C57BL/6 mice (n=3/group) for responder cell donation were allocated to one of three groups: CXCL12-coated islet transplant, non-coated islet transplant, or no treatment. 10 days after variable treatment, spleens were mechanically disrupted and filtered, and red blood cells were lyzed using M-lyse buffer (R&D Systems). Allogeneic stimulator cells from untreated BALB/c mouse spleens were similarly prepared and incubated with 20 µg/ml Mitomycin C (Sigma Aldrich) for 1 hour at 37° C., washed repeatedly with medium, and co-cultured at 37° C. and 5% $CO_2$ with responder cells for three days at a 1:1 ratio. Eighteen hours prior to the completion of the stimulation, the cells were pulsed with a 1 mM solution of bromodeoxyuridine (BrdU, BD Biosciences). After 72 hours of culture, cells were washed and subsequently stained with anti-mouse CD3 (APC-Cy7), CD8 (PerCP), and CD4 (PE-Cy7) (BD Biosciences). Cells were permeabilized with Cytofix/Cytoperm (BD Biosciences), subjected to DNase digestion (Sigma Aldrich), and stained with PE-conjugated anti-BrdU antibody (BD Biosciences). Flow cytometric analysis was performed on a LSRII (BD Biosciences) and data analyzed with FlowJo software (TreeStar) for T cells per spleen that were stimulated and that incorporated BrdU minus the number of unstimulated cells per spleen that incorporated BrdU.

Transmigration assays. Two types of migration assays were performed. First, cell migration was measured using a Boyden Chamber (96-well format, 3-µm pore; ChemoTx System, Neuro Probe Inc, Gaithersburg, Mass.) as previously described in Poznansky et al., Journal of clinical investigation, 109, 1101 (2002). For example, ~30 µL of RPMI 1640 supplemented with 0.5% FBS, along with 50 control islets or islets coated with 1 µg/ml CXCL12 (PeproTech Inc, Rocky Hill, N.J.), was added to the lower and upper chambers. 7,000 T-reg cells or CD8 T-cells, isolated with the CD4, CD25 and/or CD8 MACS separation kits, respectively (Miltenyi Biotec, Auburn, Calif.), were loaded into the upper chamber of the Boyden Chamber. After a three-hour incubation at 37° C. and 5% $CO_2$, cells on the upper surface of the membrane were removed and migrated cells in the lower chamber were counted in triplicate. Separately, migration to encapsulated islets, with or without CXCL12 incorporated into the capsules, was also measured using a Transwell system (24-well format, 3 µm pore, Corning). Briefly, 500 µl of RPMI 1640 supplemented with 0.5% FBS, alone or with 10 control or ~1 µg/ml CXCL12-incorporated capsules, was loaded into the bottom chamber. 100 µl of media, alone or with variably treated capsules, was loaded into the upper chamber along with $10^5$ cells of the desired population. Cells were incubated for 3 hours at 37° C. and 5% $CO_2$ and the number of migrated cells was counted in triplicate. For both assays, a transmigration index was calculated as the ratio between the number of cells counted in the presence of CXCL12 and in media-only controls.

Quantitation of CXCR4 expression on T-Cell subsets. Splenocytes were harvested from untreated NOD/LtJ mice and red blood cells were lysed using Mouse Erythrocyte Lysing Buffer (R&D Systems). Cells were then stained for the surface markers CD3ε, CD4, CD8α, CD25, and CXCR4 (CD184) (CD3ε: clone 145-2C11; CD4: clone RM 4-5; CD8α: clone 53-6.7; CD25: clone PC61; CXCR4: clone 2B11, BD Biosciences), fixed, permeabilized with BD Cytofix/Cytoperm (BD Biosciences) according to the manufacturer's instructions, and stained for the intracellular marker FoxP3 (clone MF23, BD Biosciences). Flow cytometry was performed on a 4 Laser LSR II (BD Biosciences). Data were analyzed using FlowJo software (Tree Star) and gating was accomplished using a fluorescence-minus-one gating strategy.

Statistical analysis. Islet graft survival between groups was compared using the Kaplan-Meier method, and the survival data were analyzed by using the GraphPad Prism 5 statistic software. Numerical variables were compared using Student's t test. A p-value below 0.05 was considered statistically significant.

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

REFERENCES

All patents, patent applications and publications mentioned in this specification are herein incorporated by reference to the same extent as if each independent patent and publication was specifically and individually indicated to be incorporated by reference. Incorporation by reference herein includes, but is not limited to:

1. N. Papeta et al., Long-term survival of transplanted allogeneic cells engineered to express a T cell chemorepellent. *Transplantation* 83, 174 (Jan. 27, 2007).
2. A. M. Shapiro et al., International trial of the Edmonton protocol for islet transplantation. *The New England journal of medicine* 355, 1318 (Sep. 28, 2006).
3. J. S. Kaddis et al., Human pancreatic islets and diabetes research. *JAMA: the journal of the American Medical Association* 301, 1580 (Apr. 15, 2009).
4. R. P. Robertson, Islet transplantation as a treatment for diabetes—a work in progress. *The New England journal of medicine* 350, 694 (Feb. 12, 2004).
5. R. B. Jalili et al., Local expression of indoleamine 2,3 dioxygenase in syngeneic fibroblasts significantly prolongs survival of an engineered three-dimensional islet allograft. *Diabetes* 59, 2219 (September, 2010).
6. V. Vaithilingam, J. Oberholzer, G. J. Guillemin, B. E. Tuch, The humanized NOD/SCID mouse as a preclinical model to study the fate of encapsulated human islets. *The review of diabetic studies: RDS* 7, 62 (Spring, 2010).
7. A. G. Mallett, G. S. Korbutt, Alginate modification improves long-term survival and function of transplanted encapsulated islets. *Tissue engineering. Part A* 15, 1301 (June, 2009).
8. N. Sakata et al., Encapsulated islets transplantation: Past, present and future. *World journal of gastrointestinal pathophysiology* 3, 19 (Feb. 15, 2012).

9. M. C. Poznansky et al., Thymocyte emigration is mediated by active movement away from stroma-derived factors. *The Journal of clinical investigation* 109, 1101 (April, 2002).
10. M. C. Poznansky et al., Active movement of T cells away from a chemokine. *Nature medicine* 6, 543 (May, 2000).
11. M. Khattar et al., Novel sphingosine-1-phosphate receptor modulator KRP203 combined with locally delivered regulatory T cells induces permanent acceptance of pancreatic islet allografts. *Transplantation* 95, 919 (Apr. 15, 2013).
12. F. Vianello, I. T. Olszak, M. C. Poznansky, Fugetaxis: active movement of leukocytes away from a chemokinetic agent. *J Mol Med (Berl)* 83, 752 (October, 2005).
13. E. Righi et al., CXCL12/CXCR4 blockade induces multimodal antitumor effects that prolong survival in an immunocompetent mouse model of ovarian cancer. *Cancer research* 71, 5522 (Aug. 15, 2011).
14. Z. Liu, J. F. Habener, Stromal cell-derived factor-1 promotes survival of pancreatic beta cells by the stabilisation of beta-catenin and activation of transcription factor 7-like 2 (TCF7L2). *Diabetologia* 52, 1589 (August, 2009).
15. A. J. Pelletier et al., Presentation of chemokine SDF-1 alpha by fibronectin mediates directed migration of T cells. *Blood* 96, 2682 (Oct. 15, 2000).
16. A. Datta et al., Differential effects of immunosuppressive drugs on T-cell motility. *American journal of transplantation: official journal of the American Society of Transplantation and the American Society of Transplant Surgeons* 6, 2871 (December, 2006).
17. L. Yu et al., Early expression of antiinsulin autoantibodies of humans and the NOD mouse: evidence for early determination of subsequent diabetes. *Proceedings of the National Academy of Sciences of the United States of America* 97, 1701 (Feb. 15, 2000).
18. G. S. Eisenbarth, Insulin autoimmunity: immunogenetics/immunopathogenesis of type 1A diabetes. *Annals of the New York Academy of Sciences* 1005, 109 (November, 2003).
19. E. Bonifacio et al., International Workshop on Lessons From Animal Models for Human Type 1 Diabetes: identification of insulin but not glutamic acid decarboxylase or IA-2 as specific autoantigens of humoral autoimmunity in nonobese diabetic mice. *Diabetes* 50, 2451 (November, 2001).
20. Y. Wang, D. J. Irvine, Engineering chemoattractant gradients using chemokine-releasing polysaccharide microspheres. *Biomaterials* 32, 4903 (July, 2011).
21. T. Yano, Z. Liu, J. Donovan, M. K. Thomas, J. F. Habener, Stromal cell derived factor-1 (SDF-1)/CXCL12 attenuates diabetes in mice and promotes pancreatic beta-cell survival by activation of the prosurvival kinase Akt. *Diabetes* 56, 2946 (December, 2007).
22. Q. Ma et al., Impaired B-lymphopoiesis, myelopoiesis, and derailed cerebellar neuron migration in CXCR4- and SDF-1-deficient mice. *Proceedings of the National Academy of Sciences of the United States of America* 95, 9448 (Aug. 4, 1998).
23. T. Netelenbos et al., Proteoglycans guide SDF-1-induced migration of hematopoietic progenitor cells. *Journal of leukocyte biology* 72, 353 (August, 2002).
24. C. A. Piccirillo, Regulatory T cells in health and disease. *Cytokine* 43, 395 (September, 2008).
25. G. Xia, M. Shah, X. Luo, Prevention of allograft rejection by amplification of Foxp3(+)CD4(+)CD25(+) regulatory T cells. *Translational research: the journal of laboratory and clinical medicine* 153, 60 (February, 2009).
26. K. J. Wood, Regulatory T cells in transplantation. *Transplantation proceedings* 43, 2135 (July-August, 2011).
27. G. Feng, K. J. Wood, A. Bushell, Interferon-gamma conditioning ex vivo generates CD25+CD62L+Foxp3+ regulatory T cells that prevent allograft rejection: potential avenues for cellular therapy. *Transplantation* 86, 578 (Aug. 27, 2008).
28. M. J. Richer, D. J. Lavallee, I. Shanina, M. S. Horwitz, Immunomodulation of antigen presenting cells promotes natural regulatory T cells that prevent autoimmune diabetes in NOD mice. *PloS one* 7, e31153 (2012).
29. D. R. Tonkin, J. He, G. Barbour, K. Haskins, Regulatory T cells prevent transfer of type 1 diabetes in NOD mice only when their antigen is present in vivo. *J Immunol* 181, 4516 (Oct. 1, 2008).
30. K. Hire, D. K. Ngo, K. M. Stewart-Maynard, B. Hering, P. Bansal-Pakala, FoxP3+, and not CD25+, T cells increase post-transplant in islet allotransplant recipients following anti-CD25+rATG immunotherapy. *Cellular immunology* 274, 83 (2012).
31. Q. Shi, J. R. Lees, D. W. Scott, D. L. Farber, S. T. Bartlett, Endogenous expansion of regulatory T cells leads to long-term islet graft survival in diabetic NOD mice. *American journal of transplantation: official journal of the American Society of Transplantation and the American Society of Transplant Surgeons* 12, 1124 (May, 2012).
32. R. S. Francis et al., Induction of transplantation tolerance converts potential effector T cells into graft-protective regulatory T cells. *European journal of immunology* 41, 726 (March, 2011).
33. D. Chen et al., CD4+CD25+ regulatory T-cells inhibit the islet innate immune response and promote islet engraftment. *Diabetes* 55, 1011 (April, 2006).
34. N. Marek et al., Coating human pancreatic islets with CD4(+)CD25(high)CD127(−) regulatory T cells as a novel approach for the local immunoprotection. *Annals of surgery* 254, 512 (September, 2011).
35. E. S. Yolcu et al., Pancreatic islets engineered with SA-FasL protein establish robust localized tolerance by inducing regulatory T cells in mice. *J Immunol* 187, 5901 (Dec. 1, 2011).
36. F. Jaafar et al., Correlation of CXCL12 expression and FoxP3+ cell infiltration with human papillomavirus infection and clinicopathological progression of cervical cancer. *The American journal of pathology* 175, 1525 (October, 2009).
37. L. Zou et al., Bone marrow is a reservoir for CD4+CD25+ regulatory T cells that traffic through CXCL12/CXCR4 signals. *Cancer research* 64, 8451 (Nov. 15, 2004).

We claim:

1. An eluting matrix suitable for implantation into a mammal, said matrix comprising at least one insulin producing cell,
    wherein said cell is encapsulated in a CXCL12-eluting porous alginate matrix which is permeable to the insulin, and further
    wherein the elution rate of CXCL12 from the matrix is from 1 ng/mL/hr to 3 ng/mL/hr so as to repel effector T-cells surrounding said matrix for a period of at least one month after implantation.

2. The eluting matrix of claim 1, wherein the elution rate of CXCL12 is 1.75 ng/mL/hr.

3. The eluting matrix of claim 1, wherein the CXCL12 is present in the matrix at a concentration of at least about 100 ng/mL.

4. The eluting matrix of claim 1, wherein the CXCL12 is present in the matrix at a concentration of between about 100 ng/mL to about 1 µg/mL.

5. The eluting matrix of claim 4, wherein the CXCL12 is present in the matrix at a concentration of between about 100 ng/mL to about 1 µg/mL for about 3 months to about 2 years after implantation.

6. The eluting matrix of claim 1, wherein the matrix has a thickness of from about 200 microns to about 500 microns.

7. The eluting matrix of claim 1, further comprising a secondary layer of cells that express a CXCL12 polypeptide.

8. The eluting matrix of claim 1, further comprising an outer layer of a CXCL12 polypeptide.

9. The eluting matrix of claim 1, wherein said at least one cell is selected from the group consisting of a myocyte, a fibroblast, a chondrocyte, an adipocyte, a fibromyoblast, an ectodermal cell, a kidney cell, a liver cell, a pancreatic cell, an intestinal cell, an osteoblast, and a hematopoietic cell.

10. The eluting matrix of claim 1, wherein said at least one cell is selected from the group consisting of a neuronal cell, a smooth muscle cell, a skeletal muscle cell, a cardiac cell, an epithelial cell, and a hepatocyte.

11. The eluting matrices of claim 1, wherein said at least one cell is a stem cell.

12. An eluting matrix suitable for implantation into a mammal, said matrix comprising at least one xenogenic islet cell capable of expressing insulin, wherein said cell is encapsulated in a CXCL12 eluting porous alginate matrix having a thickness of from 200 microns to 500 microns, and
    further wherein the elution rate of CXCL12 is from 1 ng/mL/hr to 3 ng/mL/hr thereby providing a fugetactic environment surrounding said composition which is maintained for a period of at least one month after implantation and wherein said matrix is permeable to the insulin expressed by said cell.

13. The eluting matrix of claim 12, wherein the elution rate of CXCL12 is 1.75 ng/mL/hr.

14. The eluting matrix of claim 12, wherein the CXCL12 is present in the matrix at a concentration of at least about 100 ng/mL.

15. The eluting matrix of claim 12, wherein the CXCL12 as present in the matrix at a concentration of between about 100 ng/mL to about 1 µg/mL.

16. The eluting matrix of claim 12, wherein the CXCL12 is present in the matrix at a concentration of between about 100 ng/mL to about 1 µg/mL for about 3 months to about 2 years after implantation.

17. The eluting matrix of claim 12, wherein said alginate matrix is covalently crosslinked.

18. The eluting matrix of claim 12, wherein said matrix comprise about 1.5 to about 2% w/v of a high mannuronic acid, calcium cross-linked alginate.

19. The elating matrix of claim 12, wherein said alginate matrix is comprised of alginate polymer subunits having an average molecular weight of less than 75 kDa.

20. The eluting matrix of claim 12, wherein said alginate matrix is comprised of alginate polymer subunits having an average molecular weight of about 75 kDa to about 200 kDa.

21. The eluting matrix of claim 12, wherein said alginate matrix is comprised of mannuronic acid and guluronic acid.

22. The eluting matrix of claim 21, wherein said alginate matrix comprises a mannuronic acid to guluronic acid ratio of about 1:100 to about 100.1.

23. The eluting matrix of claim 21, wherein said alginate matrix comprises a guluronic acid to mannuronic acid ratio of no more than 3:2.

* * * * *

UNITED STATES PATENT AND TRADEMARK OFFICE
CERTIFICATE OF CORRECTION

PATENT NO. : 9,775,816 B2  
APPLICATION NO. : 15/019449  
DATED : October 3, 2017  
INVENTOR(S) : Poznansky et al.

Page 1 of 1

It is certified that error appears in the above-identified patent and that said Letters Patent is hereby corrected as shown below:

In the Specification

Column 1, Line 64:
Please correct "effector cells" to read -- effector T cells --

Column 5, Lines 29-30:
Please correct "about but" to read -- about 1 μg/ml, but --

Column 7, Line 60:
Please correct "Student's test" to read -- Student's t test --

Column 9, Line 9:
Please correct "NP_001029058" to read -- NP.001029058 --

Column 10, Line 1, SEQ ID NO:3:
Please correct "pvslsyrcper" to read -- pvslsyrcpcr --

Column 26, Line 16:
Please correct "Ap-value" to read -- A p-value --

In the Claims

Column 34, Claim 15, Line 34:
Please correct "as present" to read -- is present --

Column 34, Claim 22, Line 56:
Please correct "100.1" to read -- 100:1 --

Signed and Sealed this
Tenth Day of July, 2018

Andrei Iancu
*Director of the United States Patent and Trademark Office*

SEQUENCE LISTING

<160> NUMBER OF SEQ ID NOS: 6

<210> SEQ ID NO 1
<211> LENGTH: 89
<212> TYPE: PRT
<213> ORGANISM: Homo sapiens

<400> SEQUENCE: 1

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 2
<211> LENGTH: 93
<212> TYPE: PRT
<213> ORGANISM: Homo sapiens

<400> SEQUENCE: 2

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 3
<211> LENGTH: 119
<212> TYPE: PRT
<213> ORGANISM: Homo sapiens

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Arg Gln Lys Lys Arg Lys
            100                 105                 110

Ala Ala Gln Lys Arg Lys Asn
        115

<210> SEQ ID NO 4
<211> LENGTH: 140
<212> TYPE: PRT
<213> ORGANISM: Homo sapiens

<400> SEQUENCE: 4

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Leu Ile Ser Ala Ala Pro Ala
                85                  90                  95

Gly Lys Arg Val Ile Ala Gly Ala Arg Ala Leu His Pro Ser Pro Pro
            100                 105                 110

Arg Ala Cys Pro Thr Ala Arg Ala Leu Cys Glu Ile Arg Leu Trp Pro
            115                 120                 125

Pro Pro Glu Trp Ser Trp Pro Ser Pro Gly Asp Val
        130                 135                 140

<210> SEQ ID NO 5
<211> LENGTH: 90
<212> TYPE: PRT
<213> ORGANISM: Homo sapiens

<400> SEQUENCE: 5

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Cys
                85                  90

<210> SEQ ID NO 6
<211> LENGTH: 100
<212> TYPE: PRT
<213> ORGANISM: Homo sapiens

<400> SEQUENCE: 6

Met Asn Ala Lys Val Val Val Leu Val Leu Val Leu Thr Ala Leu
1               5                   10                  15

-continued

```
Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Ile Trp Leu Tyr Gly Asn Ala
            85                  90                  95

Glu Thr Ser Arg
            100
```